United States Patent
Zhong et al.

(10) Patent No.: US 10,292,940 B2
(45) Date of Patent: May 21, 2019

(54) HYALURONIC ACID-BASED AMPHIPHILIC POLYMER, PREPARATION METHOD AND APPLICATION THEREOF

(71) Applicant: BrightGene Bio-Medical Technology Co., Ltd., Jiangsu (CN)

(72) Inventors: Zhiyuan Zhong, Jiangsu (CN); Yinan Zhong, Jiangsu (CN); Fenghua Meng, Jiangsu (CN); Jiandong Yuan, Jiangsu (CN); Yangqing Huang, Jiangsu (CN); Jianwen Chi, Jiangsu (CN)

(73) Assignee: BrightGene Bio-Medical Technology Co., Ltd. (CN)

( * ) Notice: Subject to any disclaimer, the term of this patent is extended or adjusted under 35 U.S.C. 154(b) by 29 days.

(21) Appl. No.: 15/541,771

(22) PCT Filed: Jan. 4, 2016

(86) PCT No.: PCT/CN2016/070032
§ 371 (c)(1),
(2) Date: Jul. 6, 2017

(87) PCT Pub. No.: WO2016/110228
PCT Pub. Date: Jul. 14, 2016

(65) Prior Publication Data
US 2018/0092858 A1    Apr. 5, 2018

(30) Foreign Application Priority Data
Jan. 7, 2015   (CN) .......................... 2015 1 0006737

(51) Int. Cl.
*A61K 9/51* (2006.01)
*A61K 47/36* (2006.01)
(Continued)

(52) U.S. Cl.
CPC .............. *A61K 9/5161* (2013.01); *A61K 9/51* (2013.01); *A61K 31/704* (2013.01);
(Continued)

(58) Field of Classification Search
None
See application file for complete search history.

(56) References Cited

FOREIGN PATENT DOCUMENTS

CN          104497171 A     4/2015

OTHER PUBLICATIONS

International Search Report for PCT/CN2016/070032, citing Hang (Masters Thesis) and CN 101665569; ISR dated May 23, 2017.*
(Continued)

*Primary Examiner* — Kevin S Orwig
(74) *Attorney, Agent, or Firm* — Fish & Richardson P.C.

(57) ABSTRACT

Disclosed are a hyaluronic acid-based amphiphilic polymer, preparation method and application thereof. A main chain of the amphiphilic polymer is a hydrophilic hyaluronic acid and can be employed in active targeting, and a side chain thereof is a hydrophobic group represented by Formula (1). The amphiphilic polymer can carry a small molecule anti-cancer drug. Polymer nanoparticles are obtained via chemical crosslinking, such that the nanoparticles are not readily dissociated outside a cell or in blood, thus ensuring the stability of a drug encapsulated by the nanoparticles. Upon arriving at a tumor tissue, the hyaluronic acid on a surface of the nanoparticle can immediately combine with a CD44 receptor on a surface of a tumor cell, and effectively enter the tumor cell via endocytosis mediated by the receptor, and then quickly de-crosslink to be dissociated. The drug is quickly released, obtaining an enrichment ratio at a tumor site markedly higher than that of the prior art, resulting in a highly effective treatment, and addressing deficiencies such
(Continued)

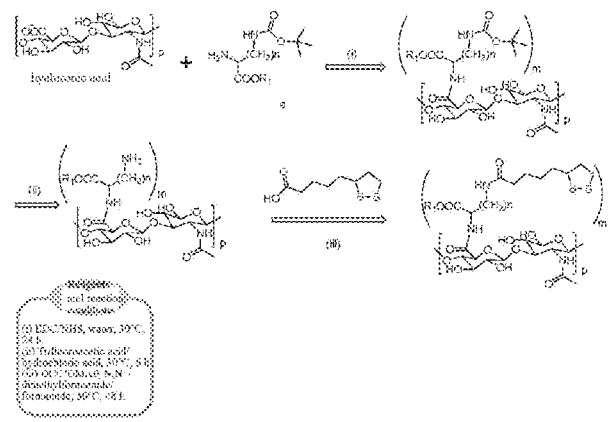

General routes of the preparation in Examples 28 to 34 as drug leakage, low carrying efficiency, low occurrence of endocytosis and slow release in a cell.

11 Claims, 9 Drawing Sheets

(51) Int. Cl.
    *C08B 37/08*     (2006.01)
    *A61K 31/704*     (2006.01)
    *A61K 47/18*     (2017.01)
    *A61K 47/20*     (2006.01)
    *A61K 31/728*     (2006.01)
    *A61K 31/795*     (2006.01)

(52) U.S. Cl.
    CPC .......... *A61K 31/728* (2013.01); *A61K 31/795* (2013.01); *A61K 47/183* (2013.01); *A61K 47/20* (2013.01); *A61K 47/36* (2013.01); *C08B 37/0072* (2013.01)

(56) References Cited

OTHER PUBLICATIONS

Extended European Search Report dated Dec. 1, 2017 in corresponding European Application No. EP16734888.

Jing Li, et al., Redox-sensitive micelles self-assembled from amphiphilic hyaluronic aciddeoxycholic acid conjugates for targeted intracellular delivery of paclitax; Biomaterials, Elsevier Science Publishers BV., Barking, GB, vol. 33, No. 7, Nov. 13, 2011 (Nov. 13, 2011), pp. 2310-2320.

Yinan Zhong, et al., Reversibly crosslinked hyaluronic acid nanoparticles for active targeting and intelligent delivery of doxorubicin to drug resistant CD44+ human breast tumor xenografts; Journal of Controlled Release, vol. 205, Jan. 14, 2015 (Jan. 14, 2015), pp. 144-154.

Yu-Ling Li, et al., Reversibly Stabilized Multifunctional Dextran Nanoparticles Efficiently Deliver Doxorubicin into the Nuclei of Cancer Cells, Angewandte Chemie International Edition, vol. 48, No. 52, Dec. 21, 2009 (Dec. 21, 2009), p. 9914-9918.

\* cited by examiner

FIG. 11: General routes of the preparation in Examples 24 to 27
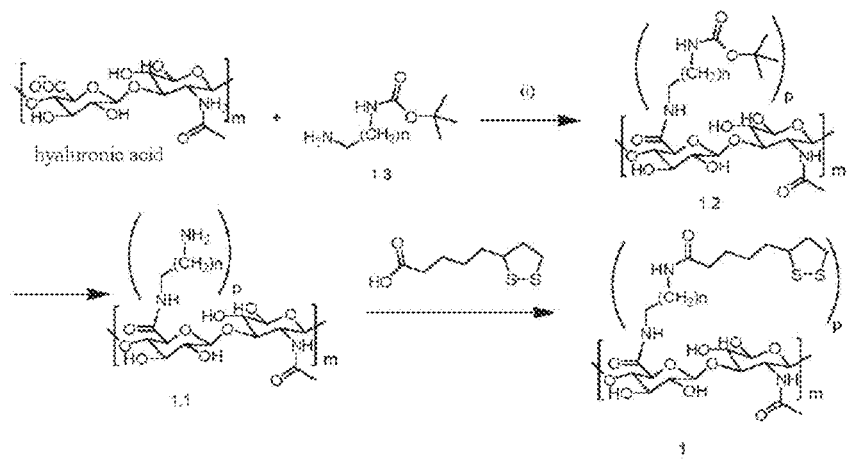
FIG. 12: General routes of the preparation in Examples 28 to 34
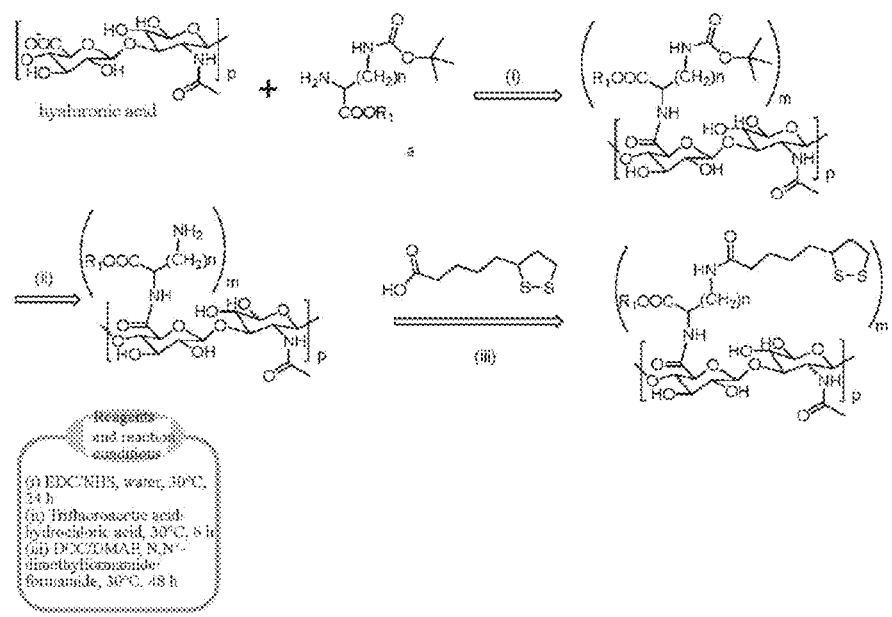

FIGs. 13A to 13D: results of tumor growth changes of DOX-loaded HA-Orn-LA crosslinked nanoparticles in LP1 tumor-bearing nude mice in Example 60
Figs. 13A: graph showing a relative tumor volume change
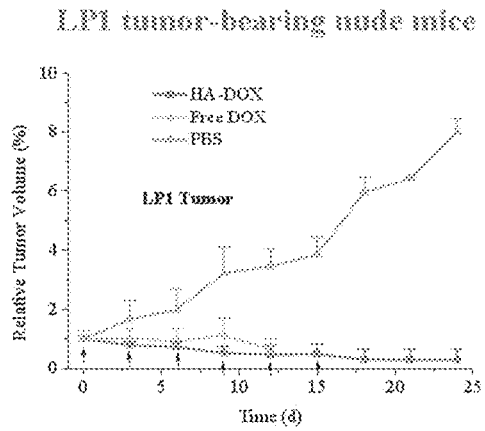
Fig. 13B: a graph showing a relative tumor volume change
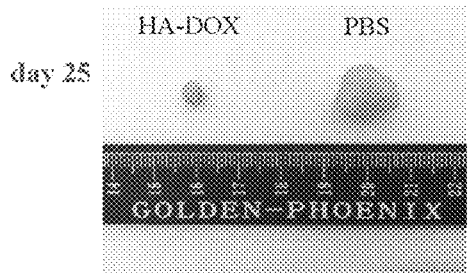
Fig. 13C: a graph showing a relative body weight change of nude mice
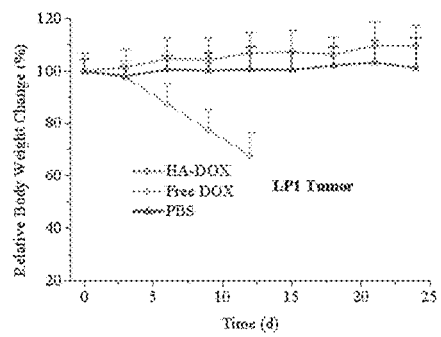

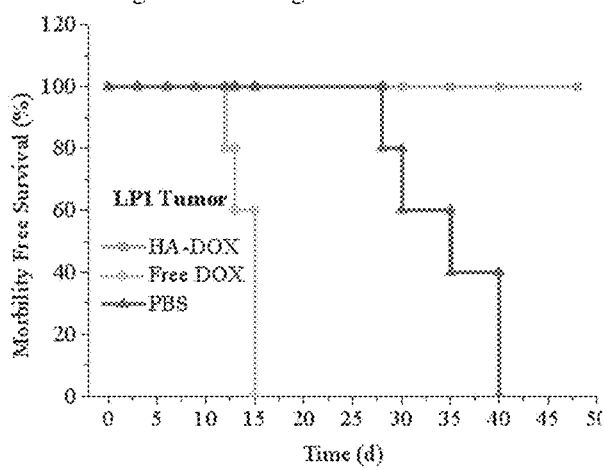
Fig. 13D: showing mice survival rate
FIG. 14: a graph showing results of circulation of DOX-loaded HA-ornithine-LA crosslinked nanoparticles in mice in Example 61
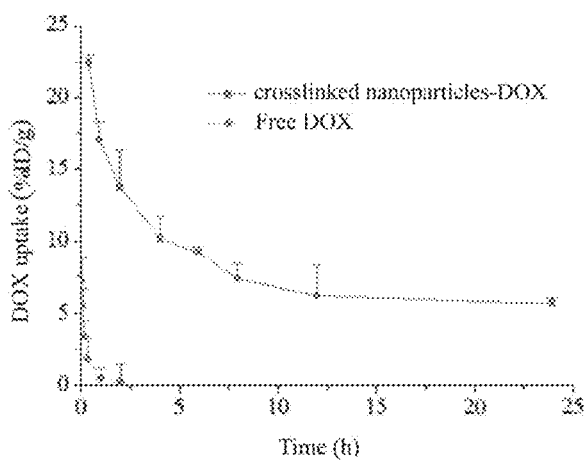

FIG. 15: a graph showing bio-distribution of DOX-loaded HA-(amino hexylamino)-LA crosslinked nanoparticles in MCF-7/ADR tumor-bearing nude mice in Example 62
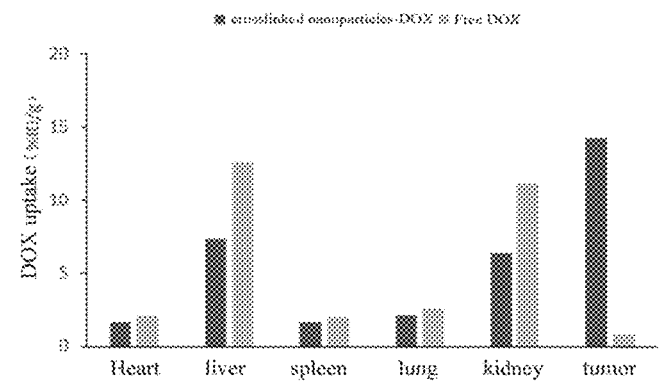

HYALURONIC ACID-BASED AMPHIPHILIC POLYMER, PREPARATION METHOD AND APPLICATION THEREOF

TECHNICAL FIELD

The present invention relates to a biodegradable polymer material and application thereof, and in particular to a hyaluronic acid-based amphiphilic polymer, nanoparticles prepared therefrom, and application thereof, which pertain to the field of pharmaceutical materials.

RELATED ART

Amphoteric natural polymers can be self-assembled in water using intermolecular interaction to form polymer nanoparticles that include an external hydrophilic layer and an internal hydrophobic layer. Nanoparticles entering a human body as a drug carrier can effectively reduce phagocytosis of macrophage in the human reticuloendothelial system (RES), can pass through the cell gap, pass through the human body's smallest capillaries and blood brain barrier (BBB) and be absorbed by cell tissue. The nanoparticle drug carrier can control the release of the drug at a targeted site, reduce the dosage of the drug, enhance the efficacy of the drug and reduce the toxicity of the drug. Ideal amphiphilic polymer nanoparticles must have good stability in blood circulation so as to avoid premature drug release and a capability of rapidly releasing the drug in tumor cells.

Jian You found that the enrichment of DOX at a tumor site was less than 5% ID/g after 6 h and 24 h after tail vein injection of doxorubicin (DOX)-loaded hollow gold nanospheres of which the surface was modified with polyethylene glycol (PEG) (see Jian You et al., Photothermal-chemotherapy with doxorubicin-loaded hollow gold nanospheres: A platform for near-infrared light-trigged drug release, Journal of Controlled Release 158 (2012) 319-328). The distribution of the existing polymer drug-loaded nanoparticles in tumors is generally 1-5% ID/g, resulting poor drug bioavailability and toxic side effects. With their surfaces modified with some targeting molecules such as polypeptides, carbohydrates, antibodies and aptamers, the polymer drug-loaded nanoparticles can effectively enter tumor cells via receptor-mediated endocytosis, and the enrichment of the nanoparticles at the tumor site can be greatly enhanced. However, this increases the cost of preparation and may have an effect on the size of the nanoparticles.

Meanwhile, a drug carrier further needs properties such as good biocompatibility, metabolites harmless to the human body, and a wide range of sources, a variety of functional groups in repeating units, being easy to be modified, so that it has great application potential in controlled release of drugs.

SUMMARY

An object of the present invention is to provide a hyaluronic acid-based amphiphilic polymer.

In order to realize the aforesaid object, a specific technical solution provided by the present invention is:

a hyaluronic acid-based amphiphilic polymer composed of a main chain and a side chain; the main chain is hyaluronic acid, and a carboxyl group in the main chain hyaluronic acid form an amide bond with the side chain; the side chain is a group represented by the following formula (1):

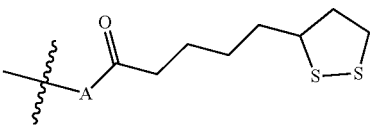

Formula (1)

Wherein, A moiety is a divalent group $^{\#}$—NH—CH(R)—$(CH_2)$n-NH—*, wherein # represents a point coupling to the main chain hyaluronic acid, and * represents a point coupling to a lipoyl group in the group of formula (1);

Wherein, group R represents H or —COOR$_1$, and R$_1$ here is H or $C_1$-$C_{10}$ aliphatic alkyl, n represents an integer of 2 to 10; and The hyaluronic acid has a molecular weight of 7 to 500 kDa; the degree of substitution of the side chain is from 5 to 40%.

In one embodiment of the present invention, n is 2, 3, 4, 5, 6, 7, 8, 9 or 10.

In one preferable embodiment, the n is 3.

In another preferable embodiment, the n is 4.

In one embodiment of the present invention, the hyaluronic acid (HA) has a molecular weight of preferably 10 to 100 kDa. In another embodiment of the present invention, the hyaluronic acid has a molecular weight of preferably 9 to 37 kDa.

In one embodiment of the present invention, the degree of substitution of the side chain is 5 to 40%. In another embodiment of the present invention, the degree of substitution of the side chain is preferably 10 to 28%.

In one embodiment of the present invention, the group R is —COOR$_1$, and R$_1$ is $C_1$-$C_8$ aliphatic alkyl. In one embodiment of the present invention, the group R is —COOR$_1$, and R$_1$ is H. Preferably, the group R is —COOR$_1$, and R$_1$, is $C_2$-$C_8$ aliphatic alkyl. Preferably, the group R is —COOR$_1$, and R$_1$ is $C_2$-$C_6$ aliphatic alkyl. Preferably, the group R is —COOR$_1$, and R$_1$ is selected from the group consisting of H, methyl, ethyl, propyl, isopropyl, n-butyl, isobutyl, tert-butyl, sec-butyl, n-pentyl, isopentyl, neopentyl, tert-amyl, hexyl, heptyl, octyl, nonyl and decyl. Preferably, the group R is —COOR$_1$, and R$_1$ is methyl.

In one embodiment of the present invention, the group R is H.

In one embodiment of the present invention, the A moiety of the side chain may be L-amino acids, derivatives thereof or analogs thereof, D-amino acids, derivatives thereof or analogs thereof, preferably L-lysine, L-lysyl ester, L-ornithine, L-ornithine ester, D-lysine, D-lysine ester, D-ornithine, or D-ornithine ester; more preferably L-lysine, L-lysine ester, L-ornithine, L-ornithine ester.

In one embodiment of the present invention, the side chain may preferably be selected from the group consisting of lysine-lipoyl, lysine ester-lipoyl, ornithine-lipoyl, and ornithine ester-lipoyl.

In one embodiment of the present invention, the side chain is lysine-lipoyl or lysine ester-lipoyl. The lysine ester-lipoyl includes but is not limited to, for example, lysine methyl ester-lipoyl, lysine ethyl ester-lipoyl, lysine propyl ester-lipoyl, lysine isopropyl ester-lipoyl, lysine n-butyl ester-lipoyl, lysine isobutyl ester-lipoyl, lysine tert-butyl ester-lipoyl, lysine sec-butyl ester-lipoyl, lysine n-amyl ester-lipoyl, lysine isoamyl ester-lipoyl, lysine hexyl ester-lipoyl, lysine heptyl ester-lipoyl, lysine octyl ester-lipoyl, lysine nonyl ester-lipoyl, lysine decyl ester-lipoyl.

In one embodiment of the present invention, the side chain is lysine methyl ester-lipoyl, of which the structural formula is as follows:

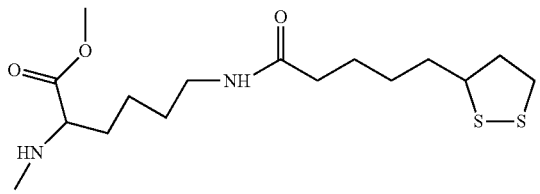 [SMILES: CNC(CCCCNC(=O)CCCCC1CCSS1)C(=O)OC]

In one embodiment of the present invention, the side chain is ornithine-lipoyl, and ornithine ester-lipoyl. The ornithine ester-lipoyl includes but is not limited to, for example, ornithine methyl ester-lipoyl, ornithine ethyl ester-lipoyl, ornithine propyl ester-lipoyl, ornithine isopropyl ester-lipoyl, ornithine n-butyl ester-lipoyl, ornithine isobutyl ester-lipoyl, ornithine tert-butyl ester-lipoyl, ornithine sec-butyl ester-lipoyl, ornithine n-amyl ester-lipoyl, ornithine isoamyl ester-lipoyl, ornithine hexyl ester-lipoyl, ornithine heptyl ester-lipoyl, ornithine octyl ornithine nonyl ester-lipoyl, ornithine decyl ester-lipoyl.

In one embodiment of the present invention, the side chain is

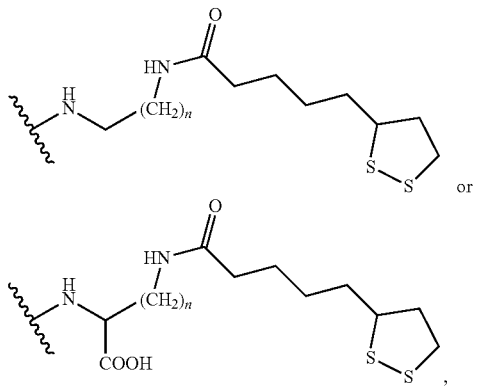

wherein n is an integer of 2 to 10; preferably, n is 2, 3, 4 or 5; more preferably, n is 2, 3 or 4.

A term "hyaluronic acid (HA)" used in the present invention is an acidic mucopolysaccharide, also known as uronic acid, hyaluronan, and its basic structure is large polysaccharides composed of two disaccharide units—D-glucuronic acid and N-acetyl glucosamine. Hyaluronic acid may consist of hundreds, thousands or even tens of thousands of disaccharide units, where D-glucuronic acid and N-acetyl glucosamine are linked by a β-1,3-glycosidic bond, and the disaccharide units are linked to each other by a β-1,4-glycosidic bond. The molecular weight of one disaccharide unit is 379.3, and according to different number of the disaccharide units composing the hyaluronic acid, the molecular weight of the hyaluronic acid may range from thousands to tens of thousands of Daltons (kDa). The structural formula of HA is as follows:

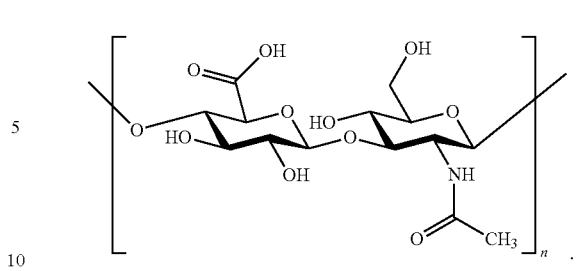

Each repeating unit in this structural formula has a molecular weight of 379.3, and each repeating unit contains one carboxyl group.

A term "$C_1$-$C_{10}$ aliphatic alkyl" used in the present invention refers to a linear or branched aliphatic alkyl group having from 1 to 10 carbon atoms. Representative examples of $C_1$-$C_{10}$ aliphatic alkyl include methyl, ethyl, propyl, isopropyl, n-butyl, isobutyl, tert-butyl, sec-butyl, n-pentyl, isopentyl, neopentyl, tert-pentyl, hexyl, heptyl, octyl, nonyl and decyl.

A term "degree of substitution" used in the present invention refers to a degree to which the hydroxyl group of —COOH in an HA molecule is substituted by the side chain. A calculation method of the degree of substitution (DS) is as follows:

Take HA-Lys and its $^1$H NMR (400 MHz, $D_2O$) spectra shown in FIG. 10 as an example, the degree of substitution can be calculated based on an area integral of peaks f and a. For example, for HA-Lys with DS of 20%, its integral area f/a is about 20%.

Another object of the present invention is to provide a method of preparing the hyaluronic acid-based amphiphilic polymer described by the present invention. The method comprises the following steps: at first, the hyaluronic acid is subjected to an amidation reaction with an N-protected amino acid, a derivative or analogue thereof, or a $C_3$-$C_{11}$ alkyl diamine, and is converted into a hyaluronic acid linked to the N-protected amino acid, a derivative or analogue thereof, or the C3-$C_{11}$ alkyl diamine via an amide bond; then deprotection is carried out, and the deprotected product undergoes an amidation reaction with lipoic anhydride, to obtain the aforesaid hyaluronic acid-based amphiphilic polymer.

In one embodiment of the present invention, the protective group of said N-protected amino acid, a derivative or analogue thereof includes but is not limited to, for example, Boc, Fmoc, Bpoc, Ddz, Cbz, Bn or Tos.

In one embodiment of the present invention, the amidation reaction between the hyaluronic acid and the N-protected amino acid, a derivative or analogue thereof, or a $C_3$-$C_{11}$ alkyl diamine is carried out with the catalysis of a coupling agent. Suitable coupling agents include, but are not limited to, for example, 1-(3-dimethylaminopropyl)-3-ethylcarbodiimide hydrochloride/N-hydroxysuccinimide (EDC/NHS) Carbodiimide-hydroxybenzotriazole (EDCI/HOBT), carbodiimide/1-hydroxy-7-azobenzotriazole (EDCI/HOAT), 2-(7-azobenzotriazole)-N,N,N',N'-tetramethyluronium hexafluorophosphate (HATU), 4-(4,6-dimethoxytriazine-2-yl)-4-methylmorpholine hydrochloride (DMTMM), benzotriazol-1-yl-oxy-tripyrrolidinyl hexafluorophosphate (PyBOP), O-benzotriazole-N,N,N',N'-tetramethyluronium tetrafluoroborate (TBTU), sodium N-hydroxy thiosuccidyl sulfonate.

In one embodiment of the present invention, the amidation reaction between the deprotected product and lipoic anhydride is carried out with the catalysis of a coupling agent. Suitable coupling agents include, but are not limited to, for example, 4-(dimethylamino) pyridine (DMAP), diisopropylethylamine (DIPEA), N-methylmorpholine, N,N-dimethylaniline, pyridine and substituted pyridine derivatives such as 2,6-dimethyl pyridine, 2,4,6-trimethyl pyridine or 4-dimethylaminopyridine.

In one embodiment of the present invention, the hyaluronic acid-based amphiphilic polymer in which the side chain is lysine methyl ester-lipoyl group may be obtained by two steps of amidation reaction: at first, under the catalysis of 1-(3-dimethylaminopropyl)-3-ethylcarbodiimide hydrochloride/N-hydroxysuccinimide (EDC/NS), a hyaluronic acid (HA) reacts with N-tert-butoxycarbonyl lysine methyl ester (H-Lys(Boc)-OMe) through amidation reaction to obtain hyaluronic acid-N-tert-butoxycarbonyl lysine methyl ester (HA-Lys(Boc)-OMe), followed by deprotection, to obtain hyaluronic acid-lysine methyl ester (HA-Lys-OMe); HA-Lys-OMe reacts with lipoic acid anhydride (LAA) through amidation reaction under catalysis of 4-(dimethylamino) pyridine (DMAP), to obtain a hyaluronic acid-based amphiphilic polymer HA-Lys-LA.

An amino acid, a derivative thereof, or a $C_3$-$C_{11}$ alkyl diamine covalently linked to a lipoyl group is introduced as a hydrophobic segment into the side chain of a hydrophilic polymer hyaluronic acid, to obtain an amphiphilic polymer; the amphiphilic polymer can be self-assembled in an aqueous solution to form nanoparticles, and then a reducing agent such as dithiothreitol (DTT) can be used to crosslink the lipoyl group to obtain crosslinked nanoparticles, which can increase stability of the nanoparticles. Wherein, the aqueous solution may be selected from pure water, phosphate buffered solution (PBS), and 4-hydroxyethyl piperazine ethanesulfonic acid (Hepes) buffer solution, etc.

Hence, another object of the present invention is to provide crosslinked nanoparticles composed of the aforesaid amphiphilic polymer, of which the outer hydrophilic layer is composed of hyaluronic acid, and the inner hydrophobic layer is composed of crosslinked five-membered rings of the side chain.

In one embodiment of the present invention, the crosslinked nanoparticles of the present invention are composed of the aforesaid amphiphilic polymer, of which the outer hydrophilic layer is composed of hyaluronic acid, and the inner hydrophobic layer is composed of crosslinked five-membered rings of lysine methyl ester-lipoyl group.

Another object of the present invention is to provide a method of preparing said crosslinked nanoparticles, comprising steps of:

(1) forming nanoparticles by self-assembly of the amphiphilic polymer, wherein the hydrophilic outer layer of the nanoparticles is composed of active targeting hyaluronic acid, and the inner hydrophobic layer is composed of side chain groups (e.g., lysine methyl ester-lipoyl group);

2) crosslinking the inner hydrophobic layer of the nanoparticles in step (1), to stabilize the structure of the nanoparticles by crosslinking of five-membered rings of lipoyl groups, to obtain crosslinked nanoparticles.

In one embodiment of the present invention, the amphiphilic polymer in the above step (1) is self-assembled in an aqueous solution to form nanoparticles having a side chain group (e.g., lysine methyl ester-lipoyl) as a hydrophobic moiety, and the nanoparticles have a particle diameter of 50-300 nm. The size is stable, and the distribution is uniform.

In one embodiment of the present invention, the cross-linking mentioned in the above step (2) can use the following method:

By using a mercapto-disulfide bond exchange reaction, a reduction-sensitive crosslinked product is obtained by exchange reaction between 1,4-dithio-D,L-threobutanol (DTT) or glutathione (GSH) and a disulfide-containing five-membered ring in the nanoparticles obtained in step (1); wherein, the amount of 1,4-dithio-D,L-threobutanol (DTT) or glutathione (GSH) is 5 to 30% of the mole number of lipoyl in the amphiphilic polymer. The nanoparticles can be crosslinked, and the stability is greatly improved compared with nanoparticles not crosslinked, and the nanoparticles do not dissociate even if diluted 1000 folds (simulated intravenous injection); and the nanoparticles are stable in an aqueous solution of 2M sodium chloride salt, and the particle size does not change.

The hydrophobic layer of the aforesaid amphiphilic polymer can load small molecular drugs and form drug-loaded nanoparticles by crosslinking to increase the stability of the drug-loaded nanoparticles. Hence, another object of the present invention is to further provide an application of the aforesaid amphiphilic polymer in the preparation of drug carriers.

Another object of the present invention is to provide a drug-loaded nanoparticle, comprising a carrier and a small molecular anticancer drug loaded on the carrier, said carrier being composed of the amphiphilic polymer according to the present invention, an outer hydrophilic layer of said carrier being composed of hyaluronic acid, and an inner hydrophobic layer of said carrier being composed of the side chain (for example, lysine methyl ester-lipoyl).

Particularly, in order to increase the stability of the drug-loaded nanoparticles in vivo, the lipoyl five-membered rings in the carrier can be crosslinked to obtain a drug-loaded nanoparticle. Thus, in a particular embodiment of the present invention there is provided a drug-loaded nanoparticle comprising a carrier and a small molecular anticancer drug loaded on the carrier, said carrier being composed of said amphiphilic polymer, an outer hydrophilic layer of said carrier being composed of hyaluronic acid, and an inner hydrophobic layer of said carrier being composed of crosslinked five-membered rings (for example, five-membered rings of lysine methyl ester-lipoyl) of the side chain.

In one embodiment of the present invention, the small molecular anticancer drug may be selected from, but not limited to, doxorubicin, paclitaxel, curcumin, docetaxel, camptothecin, mitomycin daunomycin, bleomycin, Calicheannem, Maytansinoids", Adriamycin, epirubicin or daunorubicin, etc.

In one preferable embodiment of the present invention, the drug loading efficiency of the carrier to small molecular anticancer drugs is 40% to 91%; the drug loading content ("DLC") of the drug-loaded nanoparticles is 11% to 22%.

In one preferable embodiment of the present invention, the particle size of the drug-loaded nanoparticles is 50-300 nm, and the particle size distribution is 0.02-0.30.

The present invention further provides a method of preparing the aforesaid drug-loaded nanoparticles, comprising steps of:

(1) dissolving a small molecular drug in an organic solution and then co-stirring it with an organic solution of the amphipholic polymer, and then adding phosphate buffer solution dropwise, and stirring the resulted mixture for 0.5 h, followed by dialysis, to obtain nanoparticles loading the drug;

(2) by using a mercapto-disulfide bond exchange reaction, performing chemical crosslinking on a disulfide-containing five-membered ring in the nanoparticles obtained in step (1) with 1,4-dithio-D,L-threobutanol (DTT), wherein the amount of 1,4-dithio-D,L-threobutanol (DTT) is 5 to 30% of the mole number of lipoyl in the amphiphilic polymer.

The drug-loaded nanoparticles obtained by the above method are crosslinked drug-loaded nanoparticles, which can improve the stability of the drug in blood circulation in vivo.

The small molecule drug carrier composed of the aforesaid amphiphilic polymer has both active targeting property and reduction sensitivity, can improve the stability of the drug in blood circulation in vivo, and increase the amount of drug endocytosed by tumor cells; meanwhile, the amphiphilic polymer crosslinked nanoparticles are rapidly decrosslinking and rapidly release drug in the presence of an intracellular reducing agent, thereby improving the bioavailability of the drug; moreover, the amphiphilic polymer crosslinked nanoparticles can be easily excreted. The reducing agent used for decrosslinking may be selected from mercapto-containing molecules such as 1,4-dithio-D,L-threobutanol (DTT), glutathione (GSH) or trivalent phosphorus containing compounds such as tris (2-chloroethyl) phosphate (tris (2-carboxyethyl)-phosphine, TCEP); for example, where the concentration of glutathione is 10 mM, the crosslinked nanoparticles composed of the amphiphilic polymer are rapidly decrosslinked and rapidly release drug to treat diseases.

In the present invention, a hydrophobic core of the nanoparticles composed of amphiphilic polymers is loaded with small molecular anticancer drugs; a hydrophilic shell hyaluronic acid has a tumor active targeting ability, can bind to CD44 receptor on the surface of a variety of cancer cells, and is effectively endocytosed into tumor cells by means of receptor-mediated endocytosis; besides, crosslinking can increase stability of drug-loaded nanoparticles during delivery in vivo; after entering the tumor cells, the crosslinked drug-loaded nanoparticles are sensitive to the intracellular reducing environment of the tumor cells and can be rapidly decrosslinked and release drugs, thereby effectively killing cancer cells.

Hence, another object of the present invention is to provide an application of the aforesaid drug loaded nanoparticles comprising a carrier and a small molecular anticancer drug loaded on the carrier in the preparation of an antitumor drug. In one preferable embodiment, the tumor is preferably a tumor in which the CD44 receptor is overexpressed on the cell surface.

Because of the implementation of the above-mentioned embodiments, the present invention has the following advantages compared with the prior art.

1. The present invention discloses a drug carrier based on hyaluronic acid amphiphilic polymer for the first time, which has high drug drug loading efficiency, stable in vivo circulation, high drug utilization ratio, good biocompatibility and small side effect, and can be easily excreted.

2. The hyaluronic acid based amphiphilic polymer disclosed in the present invention contains a lipoyl group as the hydrophobic part, and by means of self-assembly and crosslinking of the former, stable crosslinked nanoparticles can be obtained; said nanoparticles are not easy to dissociate outside cells and in blood, thereby ensuring stability of drugs encapsulated by the nanoparticles and increasing in vivo circulation time of the drugs; it overcomes the shortcoming of the prior art, i.e., the drug can be easily leaked in vivo and has a low transport efficiency; the nanoparticles provided in this present invention have reduction sensitivity and are decrosslinked in a reducing environment, release drugs, and effectively transfer the drugs to a target tissue.

3. The drug carrier of hyaluronic acid-based amphiphilic polymer disclosed in the present invention contains hyaluronic acid as a hydrophilic part, and it can actively target to a surface of a tumor cell and be endocytosed into tumor cells by means of receptor-mediated endocytosis, which efficiently increases the cell endocytosis capability and overcomes the problem of low cell uptake capacity for ordinary nanosized carriers.

4. The drug carrier of hyaluronic acid-based amphiphilic polymer disclosed in the present invention can effectively enter tumor cells without modification of target molecules and reaches a high enrichment rate at the tumor site; wherein, HA-Lys-LA reaches 12.71% ID/g; when the side chain is —NH—$(CH_2)_n$—NH-lipoyl, its enrichment rate at the tumor site is significantly higher than that of HA-Lys-LA (namely, HA-lysine methyl ester-LA); particularly HA-(aminohexylamino)-LA, its enrichment rate reaches 15.3% ID/g, far higher than the level of the prior art; it has high cytotoxicity for tumor cells, drug-resistant tumor cells and tumor stem cells.

5. The drug carrier disclosed in the present invention can be prepared simply, and it has good biocompatibility, metabolites harmless to the human body, and a wide range of sources, a variety of functional groups in repeating units, it is easy to be modified; and it can be rapidly decrosslinked and dissociated at a tumor site so that the drug is rapidly released, thereby producing efficient therapeutic effect, so it has great application potential in controlled release of drugs area.

6. For the drug carrier of hyaluronic acid-based amphiphilic polymer disclosed in the present invention, particularly when the side chain of the hyaluronic acid based amphiphilic polymer is ornithine-lipoyl, HA-DOX has a very significant therapeutic effect on LP1 tumors. As shown by FIG. 13A, as compared with a phosphate buffer solution (PBS) group, after treatment with HA-DOX for 25 days, 2/5 tumor volume disappears; although a free drug group can also achieve a similar effect, mice are not tolerated for the free drug, and the body weight of the mice in the free drug group significantly decreases after about 12 days, whereas the HA-DOX group and the PBS group had a close effect on the body weight of the mice, and the weight change is still not significant after administration for 24 days (as shown by FIG. 13C); with reference to FIGS. 13A and 13D, it can be further found that all mice die after administration of free drug for about 12 to 15 days, while the mice in the HA-DOX group survive for more than 50 days, which indicates that HA-DOX has a high treatment effect on mice LP1 tumor and meanwhile the mice has good tolerance to HA-DOX.

7. The drug carrier of hyaluronic acid-based amphiphilic polymer disclosed in the present invention, particularly drug-loaded HA-Ornithine methyl ester-LA crosslinked nanoparticles have high enrichment rate at a tumor site and a long circulation time period in the body of mice.

8. The nanoparticles of hyaluronic acid-based amphiphilic polymer, particularly when the side chain is ornithine, ornithine ester or its derivative-lipoyl, —NH—$(CH_2)_n$—NH-lipoyl, the resulting nanoparticles have small particle size and an average particle size distribution of 0.15 or less. Moreover, a drug-loaded crosslinked nanoparticle prepared therefrom has a drug drug loading efficiency and drug loading content which are both significantly improved compared with HA-lysine methyl ester-LA. When the theoretical drug loading content is 20%, the drug loading efficiency of HA-lysine methyl ester-LA ($M_{nHA}$=35 kDa, DS=10%) crosslinked nanoparticles to doxorubicin is 54.5%, and the actual drug loading content is 12%. In the condition of identical drug loading content, HA-ornithine methyl ester-LA ($M_{nHA}$=35 kDa, DS=10%), the drug loading efficiency of crosslinked nanoparticles to doxoruhicin is 79.57%, and the actual drug loading content is as high as 15.56%, HA-lysine-LA ($M_{nHA}$=35 kDa, DS=10%), the drug loading efficiency of crosslinked nanoparticles to doxorubicin is 81.5%, and the actual drug loading content is as high as 16.38%.

BRIEF DESCRIPTION OF THE DRAWINGS

FIG. 11 shows general routes of the preparation in Examples 24 to 27;

FIG. 12 shows general routes of the preparation in Examples 28 to 34;

FIGS. 13A to 13D show results of tumor growth changes in LP1 tumor (multiple myeloma)-bearing nude mice treated with DOX-loaded HA-Om-LA (HA-ornithine-LA) crosslinked nanoparticles in Example 60; wherein FIGS. 13A and 13B show a relative tumor volume change, FIG. 13C shows a relative change in body weight of nude mice, FIG. 13D shows a mice survival rate.

FIG. 14 is a graph showing results of circulation of DOX-loaded HA-ornithine methyl ester-LA crosslinked nanoparticles in mice in Example 61;

FIG. 15 is a graph showing bio-distribution of DOX-loaded HA-(amino hexylamino)-LA crosslinked nanoparticles in MCF-7/ADR tumor-bearing nude mice in Example 62.

DETAILED DESCRIPTION

The present invention is further described below with reference to the drawings and Examples.

Example 1 Synthesis of a Polymer Hyaluronic Acid-Lysine Methyl Ester-Lipoic Acid (Named HA-Lys-LA) ($M_{nHA}$=35 kDa, DS=10%)

Figure 1:
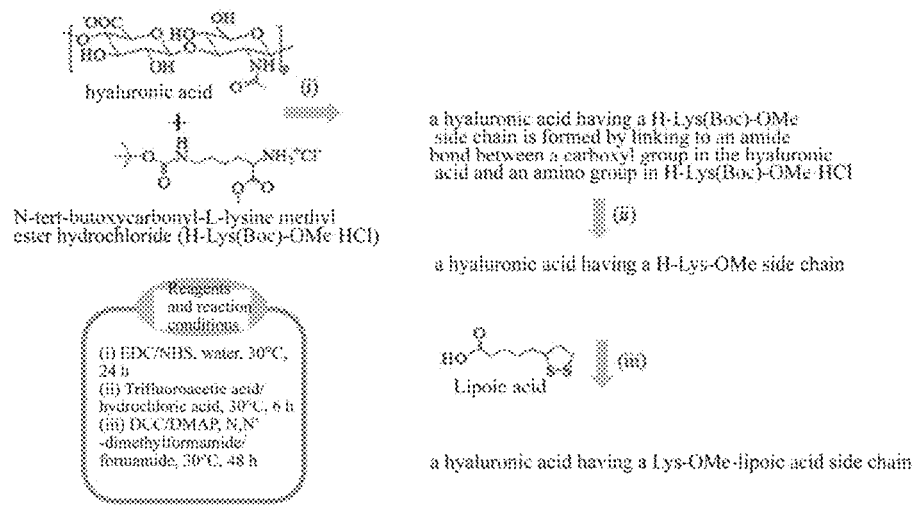
FIG. 1 is diagram showing a synthetic route of a polymer HA-Lys-LA in the Examples.

FIG. 1 is diagram showing a synthetic route of a polymer HA-Lys-LA in the Examples. Firstly, triethylamine (85 mg, 0.84 mmol) was added to a solution of N-tert-butoxycarbonyl-L-lysine methyl ester hydrochloride (H-Lys(Boc)-OMe.HCl) (240 mg, 0.80 mmol)/anhydrous methanol (2 mL) at room temperature. The mixture was stirred for 1 h. 1-(3-dimethylaminopropyl)-3-ethylcarbodi-imide hydrochloride (EDC) (460 mg, 2.40 mmol), N-hydroxysuccinimide (NHS) (140 mg, 1.22 mmol) and hydrochloride-removed N-tert-butoxycarbonyl-L-lysine methyl ester hydrochloride (H-lys(Boc)-OMe)/methanol solution were in order added to an aqueous solution of HA (300 mg, 0.79 mmol carboxyl group) (6 mL). Adjusted the pH of the mixture to 8.5 and then stirred for 24 h at room temperature. The resulted hyaluronic acid tert-buoxycarbonyl lysine methyl ester (HA-Lys(OMe)-Boc) adduct was isolated by extensive dialysis, followed by lyophilization. Then, totally 6 mL of trifluoroacetic acid/2M hydrochloric acid (v/v 1:1) were in order added to the obtained solid HA-Lys(OMe)-Boc. The reaction was carried out with stirring for 6 h. After the deprotection finished, the solution was adjusted to pH 7.0, followed by dialysis and lyophilization. Yield: 92%. The results of NMR showed that the structure was hyaluronic acid-lysine methyl ester (HA-Lys (OMe)), in which the degree of substitution (DS) of lysine methyl ester (Lys (OMe)) was 10%.

Lipoic acid (12 mg, 58 µmol) was dissolved in 2.0 mL of dichloromethane and added to a 25 mL Schlenk vacuum sealed flask, and N,N-dicyclohexylcarbodiimide (DCC) (6 mg, 29 µmol amino) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 ml of N,N'-dimethylformamide having undergone anhydrous treatment. HA-Lys (OMe) (60 mg, 27 µmol amino) dissolved in 5 mL formamide, the lipoic acid anhydride, and 4-ditmethylaminopyridine (DMAP) (4 mg, 33 µmol) dissolved in 0.5 mL of N,N'-dimethylformamide were in order added to a 50 mL three-necked flask under a nitrogen atmosphere; the reactor was placed in an 30° C. oil bath and stirred for 48 h, followed by dialysis in water/ethanol (1/1) and water in order, and lyophilized. Yield: 95%. The results of NMR showed that the structure was hyaluronic acid-lysine methyl ester-lipoic acid (HA-Lys-LA), in which the degree of substitution (DS) of lysine methyl ester-lipoyl was 10%.

Example 2 Synthesis of a Polymer HA-Lys-LA ($M_{nHA}$=35 kDa, DS=5%)

Firstly, triethylamine (42 mg, 042 mmol) was added to a solution of H-Lys(Boc)-OMe.HCl (120 mg, 0.40 mmol)/anhydrous methanol (2 mL) at room temperature. The mixture was stirred for 1 h. EDC (460 mg, 2.40 mmol), NHS (140 mg, 1.22 mmol) and hydrochloride-removed H-Lys(Boc)-OMe)/methanol solution were in order added to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-Lys(OMe)-Boc. Totally 6 mL of trifluoroacetic acid/2M hydrochloric acid (v/v 1:1) were in order added to the obtained solid HA-Lys(OMe)-Boc. The reaction was carried out with stirring for 6 h. After the deprotection finished, the solution was adjusted to pH 7.0, followed by dialysis and lyophilization. Yield: 89%. The results of NMR showed that the structure was HA-Lys (OMe), in which the degree of substitution (DS) of Lys (OMe) was 5%.

Lipoic acid (12 mg, 58 µmol) was dissolved in 2.0 mL of dichloromethane and added to a 25 mL Schlenk vacuum sealed flask, and DCC (6 mg. 29 µmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Lys (OMe) (60 mg, 14 µmol amino) dissolved in 5 mL formamide, the lipoic acid anhydride, and 4-dimethylaminopyridine (4 mg, 33 µmol) dissolved in 0.5 mL of N,N'-dimethylformamide were in order added to a 50 mL three-necked flask under a nitrogen atmosphere; the reactor was placed in an 30° C. oil bath and stirred for 48 h, followed by dialysis in water/ethanol (1/1) and water in order, and lyophilized. Yield: 93%. The results of NMR showed that the structure was HA-Lys-LA, in which the degree of substitution (DS) of lysine methyl ester-lipoyl was 5%.

Example 3 Synthesis of a Polymer HA-Lys-LA ($M_{nHA}$=35 kDa, DS=28%)

Firstly, triethylamine (42 mg, 0.42 mmol) was added to a solution of H-Lys(Boc)-OMe.HCl (480 mg, 1.58 mmol)/anhydrous methanol (2 mL) at room temperature. The mixture was stirred for 1 h. EDC (460 mg, 2.40 mmol), NHS (140 mg, 1.22 mmol) and hydrochloride-removed H-Lys(Boc)-OMe)/methanol solution were in order added to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-Lys(OMe)-Boc. Totally 6 mL of trifluoroacetic acid/2M hydrochloric acid (v/v 1:1) were in order added to the obtained solid HA-Lys(OMe)-Boc. The reaction was carried out with stirring for 6 h. After the deprotection finished, the solution was adjusted to pH 7.0, followed by dialysis and lyophilization. Yield: 90%, The results of NMR showed that the structure was HA-Lys (OMe), in which the degree of substitution (DS) of Lys (OMe) was 28%.

Lipoic acid (32 mg, 152 µmol) was dissolved in 2.0 mL of dichloromethane and added to a 25 mL Schlenk vacuum sealed flask, and DCC (16 mg, 76 µmol) dissolved in 1.0 mL of dichloromethane was added to the sealed flask under a nitrogen atmosphere, the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Lys (OMe) (60 mg, 76 µmol amino) dissolved in 5 mL formamide, the lipoic acid anhydride, and 4-dimethylaminopyridine (10 mg, 83 µmol) dissolved in 0.5 mL of N,N'-dimethylformamide were in order added to a 50 mL three-necked flask under a nitrogen atmosphere; the reactor was placed in an 30° C. oil bath and stirred for 48 h, followed by dialysis in water/ethanol (1/1) and water in order, and lyophilized. Yield: 91%, The results of NMR showed that the structure was HA-Lys-LA, in which the degree of substitution (DS) of lysine methyl ester-lipoyl was 28%.

Example 4 Synthesis of a Polymer HA-Lys-LA ($M_{nHA}$=8.9 kDa, DS=12%)

Firstly, triethylamine (85 mg, 0.84 mmol) was added to a solution of H-Lys(Boc)-OMe.HCl (240 mg, 0.80 mmol)/anhydrous methanol (2 mL) at room temperature. The mixture was stirred for 1 h. EDC (460 mg, 2.40 mmol), NHS (140 mg, 1.22 mmol) and hydrochloride-removed H-Lys(Boc)-OMe)/methanol solution were in order added to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-Lys(OMe)-Boc. Totally 6 mL of trifluoroacetic acid/2M hydrochloric acid (v/v 1:1) were in order added to the obtained solid HA-Lys(OMe)-Boc. The reaction was carried out with stirring for 6 h. After the deprotection finished, the solution was adjusted to pH 7.0, followed by dialysis and lyophilization. Yield: 92%. The results of NMR showed that the structure was HA-Lys (OMe), in which the degree of substitution (DS) of Lys (OMe) was 12%.

Lipoic acid (15 mg, 70 µmol) was dissolved in 2.0 mL of dichloromethane and added to a 25 mL Schlenk vacuum sealed flask, and DCC (7 mg, 35 µmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Lys (OMe) (60 mg, 32 µmol amino) dissolved in 5 mL formamide, the lipoic acid anhydride, and 4-dimethylaminopyridine (5 mg, 40 µmol) dissolved in 0.5 mL of N,N'-dimethylformamide were in order added to a 50 mL three-necked flask under a nitrogen atmosphere; the reactor was placed in an 30° C. oil bath and stirred for 48 h, followed by dialysis in water/ethanol (1/1) and water in order, and lyophilized. Yield: 94%. The results of NMR showed that the structure was HA-Lys-LA, in which the degree of substitution (DS) of lysine methyl ester-lipoyl was 12%.

Example 5 Synthesis of a Polymer HA-Lys-LA ($M_{nHA}$=8.91 kDa, DS=10%)

Firstly, triethylamine (85 mg, 0.84 mmol) was added to a solution of H-Lys(Boc)-OMe.HCl (240 mg, 0.80 mmol)/anhydrous methanol (2 mL) at room temperature. The mixture was stirred for 1 h. EDC (460 mg, 2.40 mmol), NHS (140 mg, 1.22 mmol) and hydrochloride-removed H-Lys(Boc)-OMe)/methanol solution were in order added to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-Lys(OMe)-Boc. Totally 6 mL of trifluoroacetic acid/2M hydrochloric acid (v/v 1:1) were in order added to the obtained solid HA-Lys (OMe)-Boc. The reaction was carried out with stirring for 6 h. After the deprotection finished, the solution was adjusted to pH 7.0, followed by dialysis and lyophilization, to give HA-Lys (OMe).

Lipoic acid (12 mg, 58 μmol) was dissolved in 2.0 mL of dichloromethane and added to a 25 mL Schlenk vacuum sealed flask, and DCC (0.384 g, 1.86 mmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Lys (OMe) (60 mg, 27 μmol amino) dissolved in 5 mL formamide, and the lipoic acid anhydride, and 4-dimethylaminopyridine (4 mg, 33 μmol) dissolved in 0.5 mL of N,N'-dimethylformamide were in order added to a 50 mL three-necked flask under a nitrogen atmosphere; the reactor was placed in an 30° C. oil bath and stirred for 48 h, followed by dialysis in water/ethanol (1/1) and water in order, and lyophilized. Yield: 95%. The results of NMR showed that the structure was HA-Lys-LA, in which the degree of substitution (DS) of lysine methyl ester-lipoyl was 10%.

Example 6 Synthesis of a Polymer HA-Lys-LA ($M_{nHA}$=100 kDa, DS=10%)

Firstly, triethylamine (85 mg, 084 mmol) was added to a solution of H-Lys(Boc)-OMe.HCl (240 mg, 0.80 mmol)/ anhydrous methanol (2 mL) at room temperature. The mixture was stirred for 1 h. EDC (460 mg, 2.40 mmol), NHS (140 mg, 1.22 mmol) and Hydrochloride-removed H-Lys (Boc)-OMe)/methanol solution were in order added to an aqueous solution of HA (300 mg, 079 mmol carboxyl group) (6 mL). The solution was adjusted to pH 8.5. The mixture was stirred for 24 h at room temperature, followed by dialysis and lyophilization, to obtain HA-Lys(OMe)-Boc. Totally 6 mL of trifluoroacetic acid/2M hydrochloric acid (v/v 1:1) were added in order to the obtained solid HA-Lys (OMe)-Boc. The reaction was carried out with stirring for 6 h. After the deprotection finished, the solution was adjusted to pH 7.0, followed by dialysis and lyophilization. Yield: 92%. The results of NMR showed that the structure was HA-Lys (OMe), in which the degree of substitution (DS) of Lys (OMe) was 10%.

Lipoic acid (12 mg, 58 μmol) was dissolved in 2.0 mL of dichloromethane and added to a 25 mL Schlenk vacuum sealed flask, and DCC (6 mg, 29 μmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Lys (OMe) (60 mg, 27 μmol amino) dissolved in 5 ml formamide, the lipoic acid anhydride, and 4-dimethylaminopyridine (4 mg, 33 μmol) dissolved in 0.5 mL of N,N'-dimethylformamide were in order added to a 50 mL three-necked flask under a nitrogen atmosphere; the reactor was placed in an 30° C. oil bath and stirred for 48 h, followed by dialysis in water/ethanol (1/1) and water in order, and lyophilized. The results of NMR showed that the structure was HA-Lys-LA, in which the degree of substitution (DS) of lysine methyl ester-lipoyl was 10%.

Example 7 Synthesis of a Polymer HA-Lys-LA ($M_{nHA}$=300 kDa, DS=10%)

Firstly, triethylamine (85 mg, 0.84 mmol) was added to a solution of H-Lys(Boc)-OMe.HCl (240 mg, 0.80 mmol)/ anhydrous methanol (2 mL) at room temperature. The mixture was stirred for 1 h. EDC (460 mg, 2.40 mmol), NHS (140 mg, 1.22 mmol) and Hydrochloride-removed H-Lys (Boc)-OMe)/methanol solution were added in order to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-Lys(OMe)-Boc. Totally 6 mL of trifluoroacetic acid/2M hydrochloric acid (v/v 1:1) were added in order to the obtained solid HA-Lys (OMe)-Boc. The reaction was carried out with stirring for 6 h. After the deprotection finished, the solution was adjusted to pH 7.0, followed by dialysis and lyophilization. Yield: 92%. The results of NMR showed that the structure was HA-Lys (OMe), in which the degree of substitution (DS) of Lys (OMe) was 10%.

Lipoic acid (12 mg, 58 μmol) was dissolved in 2.0 mL of dichloromethane and added to a 25 mL Schlenk vacuum sealed flask, and DCC (6 mg, 29 μmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Lys (OMe) (60 mg, 27 μmol amino) dissolved in 5 mL formamide, the lipoic acid anhydride and 4-dimethylaminopyridine (4 mg, 33 μmol) dissolved in 0.5 mL of N,N'-dimethylformamide were in order added to a 50 mL three-necked flask under a nitrogen atmosphere; the reactor was placed in an 30° C. oil bath and stirred for 48 h, followed by dialysis in water/ethanol (1/1) and water in order, and lyophilized. Yield: 95%. The results of NMR showed that the structure was HA-Lys-LA, in which the degree of substitution (DS) of lysine methyl ester-lipoyl was 10%.

Example 8 Preparation of HA-Lys-LA ($M_{nHA}$=35 kDa, DS=10%) Nanoparticles

Polymer HA-Lys-LA nanoparticles were prepared by dialysis. The detailed process was as follows: 5 mg of a polymer HA-Lys-LA (DS=10%) was dissolved in 1 mL formamide, and 4.0 mL of PBS (10 mM, pH 7.4) was added dropwise thereto at 25° C. under stirring. After the resulting solution was stirred for 1 h, it was loaded into a previously prepared dialysis bag (SPECTRA/POR, MWCO: 3500) and dialyzed against PBS solution (PBS) (10 mM, pH 7.4) for 24 h. The average particle size of the nanoparticles was 198 nm and the particle size distribution was 0.11.

Example 9 Preparation of HA-Lys-LA ($M_{nHA}$=35 kDa, DS=5%) Nanoparticles

Polymer HA-Lys-LA nanoparticles were prepared by dialysis. The detailed process was as follows: 5 mg of a polymer HA-Lys-LA (DS=5%) was dissolved in 1 mL formamide, and 4.0 mL of PBS (10 mM, pH 7.4) was added dropwise thereto at 25° C. under stirring. After the resulting solution was stirred for 1 h, it was loaded into a previously prepared dialysis bag (SPECTRA/POR, MWCO: 3500) and dialyzed against PBS (10 mM, pH 7.4) for 24 h. The average particle size of the nanoparticles was 237 nm and the particle size distribution was 0.23.

Example 10 Preparation of HA-Lys-LA ($M_{nHA}$=35 kDa, DS=28%) Nanoparticles Polymer HA-Lys-LA nanoparticles were prepared by dialysis. The detailed process was as follows: 5 mg of a polymer HA-Lys-LA (DS=28%) was dissolved in 1 mL formamide, and 4.0 mL of PBS (10 mM, pH 7.4) was added dropwise thereto at 25° C. under stirring. After the resulting solution was stirred for 1 h, it was loaded into a previously prepared dialysis bag (SPECTRA/POR, MWCO: 3500) and dialyzed against PBS (10 mM, pH 7.4) for 24 h. The average particle size of the nanoparticles was 178 nm and the particle size distribution was 0.13.

Example 11 Preparation of HA-Lys-LA ($M_{nHA}$=8.9 kDa, DS=5%) Nanoparticles Polymer HA-Lys-LA nanoparticles were prepared by dialysis. The detailed process was as follows: 5 mg of a polymer HA-Lys-LA (DS=5%) was dissolved in 1 mL formamide, and 4.0 mL of PBS (10 mM, pH 7.4) was added dropwise thereto at 25° C. under stirring. After the resulting solution was stirred for 1 h, it was loaded into a previously prepared dialysis bag (SPECTRA/POR, MWCO: 3500) and dialyzed against PBS (10 mM, pH 7.4) for 24 h. The average particle size of the nanoparticles was 203 nm and the particle size distribution was 0.25.

Example 12 Preparation of HA-Lys-LA ($M_{nHA}$=8.9 kDa, DS=13%) Nanoparticles Polymer HA-Lys-LA nanoparticles were prepared by dialysis. The detailed process was as follows: 5 mg of a polymer HA-Lys-LA (DS=13%) was dissolved in 1 mL formamide, and 4.0 mL of PBS (10 mM, pH 7.4) was added dropwise thereto at 25° C. under stirring. After the resulting solution was stirred for 1 h, it was loaded into a previously prepared dialysis bag (SPECTRA/POR, MWCO: 3500) and dialyzed against PBS (10 mM, pH 7.4) for 24 h. The average particle size of the nanoparticles was 185 nm and the particle size distribution was 0.09.

Example 13 Preparation of HA-Lys-LA ($M_{nHA}$8.9 kDa, DS=25%) Nanoparticles Polymer HA-Lys-LA nanoparticles were prepared by dialysis. The detailed process was as follows: 5 mg of a polymer HA-Lys-LA (DS=25%) was dissolved in 1 mL formamide, and 4.0 mL of PBS (10 mM, pH 7.4) was added dropwise thereto at 25° C. under stirring. After the resulting solution was stirred for 1 h, it was loaded into a previously prepared dialysis bag (SPECTRA/POR, MWCO: 3500) and dialyzed against PBS (10 mM, pH 7.4) for 24 h. The average particle size of the nanoparticles was 169 nm and the particle size distribution was 0.10.

Example 14 Crosslinking of HA-Lys-LA ($M_{nHA}$=35 kDa, DS=5%) Nanoparticles In order to obtain crosslinked polymer nanoparticles, a solution of the above-formed polymer nanoparticles (0.5 mg/ml, 2 ml) was adjusted to pH 8.5, 4 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted DTT. The crosslinked nanoparticles had a size of 219 nm and a particle size distribution of 0.27.

Figure 2:
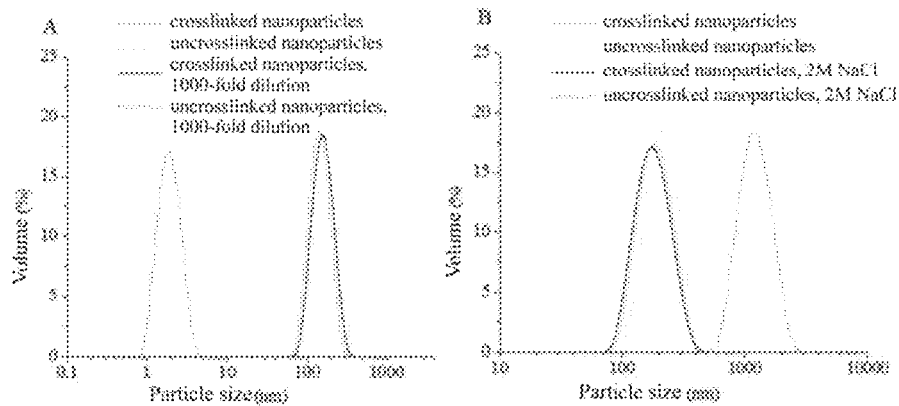
FIG. 2 is a graph showing results of the size change of HA-Lys-LA crosslinked nanoparticles under high dilution and high salinity conditions in Example 15.

Example 15 Crosslinking of HA-Lys-LA ($M_{nHA}$=35 kDa, DS=10%) Nanoparticles In order to obtain crosslinked polymer nanoparticles, a solution of the above-formed polymer nanoparticles (0.5 mg/ml, 2 ml) was adjusted to pH 8.5, 7 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted FIG. 2 shows results of the size change of HA-Lys-LA crosslinked nanoparticles under high dilution and high salinity conditions. It can be seen that the crosslinked nanoparticles had a size of 175 nm and a particle size distribution of 0.12, and that they had significant stability against high dilution (simulated intravenous injection) and high salinity (2M).

Example 16 Crosslinking of HA-Lys-LA ($M_{nHA}$=35 kDa, DS=28%) Nanoparticles In order to obtain crosslinked polymer nanoparticles, a solution of the above-formed polymer nanoparticles (0.5 mg/ml, 2 ml) was adjusted to pH 8.5, 20 mL, of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted DTT. The crosslinked nanoparticles had a size of 152 nm and a particle size distribution of 0.16.

Example 17 Crosslinking of HA-Lys-LA ($M_{nHA}$=8.9 kDa, DS=5%) Nanoparticles In order to obtain crosslinked polymer nanoparticles, a solution of the above-formed polymer nanoparticles (0.5 mg/ml, 2 ml) was adjusted to pH 8.5, 4 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted DTT. The crosslinked nanoparticles had a size of 199 nm and a particle size distribution of 0.23.

Example 18 Crosslinking of HA-Lys-LA ($M_{nHA}$=8.9 kDa, DS=13%) Nanoparticles In order to obtain crosslinked polymer nanoparticles, a solution of the above-formed polymer nanoparticles (0.5 mg/ml, 2 ml) was adjusted to pH 8.5, 7 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted DTT. The crosslinked nanoparticles had a size of 164 nm and a particle size distribution of 0.11.

Example 19 Crosslinking of HA-Lys-LA ($M_{nHA}$=8.9 kDa, DS=25%) Nanoparticles In order to obtain crosslinked polymer nanoparticles, a solution of the above-formed polymer nanoparticles (0.5 mg/ml, 2 ml) was adjusted to pH 8.5, 20 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted DTT. The crosslinked nanoparticles had a size of 148 nm and a particle size distribution of 0.23.

Example 20 Decrosslinking the Crosslinked Polymer Nanoparticles of HA-Lys-LA ($M_{nHA}$=35 kDa, DS=10%) by Excess Glutathione Under nitrogen protection, weighed glutathione (GSH) was added to a glass sample cell of 2.0 ml of HA-Lys-LA polymer crosslinked nanoparticles (0.001 mg/ml) so that the final glutathione concentration was 10 mM, and a parallel control sample was also prepared without glutathione; then the glass sample cell was sealed with a rubber stopper and shaken evenly and was placed in a 37° C. thermostat shaker (200 rpm). The particle size of the particles was tracked by dynamic laser light scattering. (DLS) at 37° C. for a selected time period. The results showed that the particle size of the crosslinked nanoparticles increased from the original 175 nm to several thousand nanometers after being affected by 10 mM glutathione for 12 h, and that the particle size decreased to several nanometers after dilution 1000 times, indicating that the crosslinked nanoparticles were decrosslinked.

Example 21 Loading of Small Molecular Anticancer Drug Doxorubicin and Its Glutathione-Triggered Release A solution of HA-Lys-LA ($M_{nHA}$=35 kDa, DS=5%, 10%, 28%)/formamide (5 mg/mL, 1 mL) was mixed with doxorubicin (DOX)/dimethylsulfoxide (5 mg/mL, 0.25 mL) under stirring for 1 h, and 4 ml of PBS was added dropwise to the mixture under stirring at 25° C. After being stirred for 1 h, the resulting solution was loaded into a previously prepared dialysis bag (SPECTRA/POR, MWCO: 3500) and dialyzed against PBS, to form a solution of drug-loaded polymer nanoparticles.

The formed drug-loaded polymer nanoparticle solution was taken in half volume and was adjusted to pH 8.5. 17.5 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The crosslinked drug-loaded nanoparticles were dialyzed against PBS to remove the unreacted DTT.

The DOX-loaded crosslinked nanoparticles were 100-fold diluted with PBS (10 mM, pH 7.4) and divided into two portions: an equal volume of PBS of GSH (10 mM) was added to one portion, and an equal volume of pure PBS was added to the other portion at 37° C. These solutions were immediately transferred to a dialysis bag and placed in a 37° C. thermostat shaker (200 rpm). The former was immersed in 25 mL of PBS having the same GSH concentration at the same temperature, and the latter was immersed in 25 mL, of PBS (20 mM) at the same temperature; after a given time period, 6 mL of dialysate outside the dialysis bag was taken to determine its fluorescence intensity, and 6 mL of a corresponding fresh solution was added to the outside of the dialysis bag.

Determination of drug loading efficiency of DOX in polymer nanoparticles: a certain amount of crosslinked and uncrosslinked drug-loaded nanoparticles solutions were taken, and the water in the solution was removed by a freeze-drying method; then 0.5 mL of formamide was added thereto, and the freeze-dried solid was fully fused with ultrasound for 1 h; 20 ml of the resulting solution was taken, to which 3 ml of formamide was added; after fluorescence test, the drug loading efficiency and drug loading content were calculated with reference to a standard curve of doxorubicin.

Drug loading efficiency=(weight of loaded doxorubicin in nanoparticles/weight of doxorubicin in feed)×100%

Drug loading content=(weight of loaded doxorubicin in nanoparticles/total weight of the blank nanoparticles and doxorubicin in feed)×100%

When the theoretical drug loading content is 20%, the drug loading efficiency of HA-lys-LA$_{10}$ crosslinked nanoparticles to doxorubicin was 54.5%, and the actual drug loading content was 12%.

Figure 3:
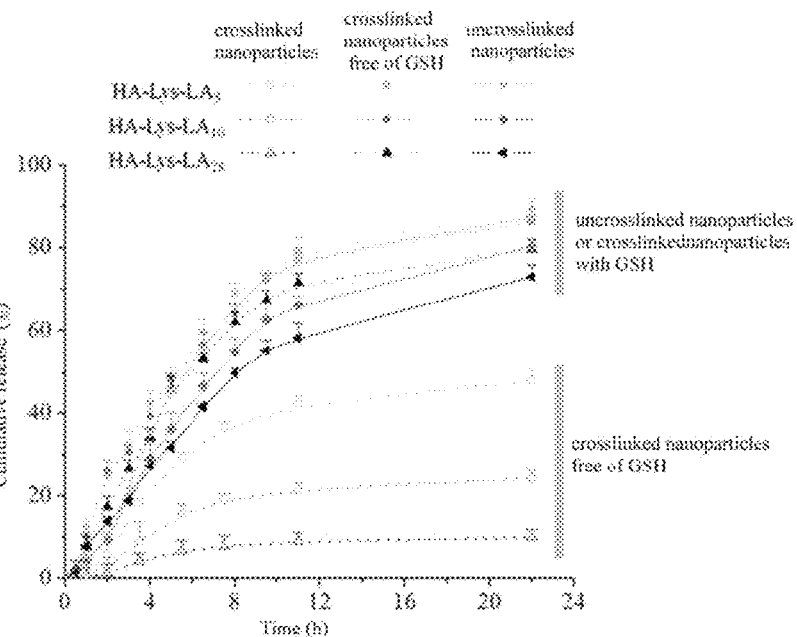
FIG. 3 is a graph showing in vitro release results of DOX-loaded HA-Lys-LA crosslinked nanoparticles under the trigger of glutathione in Example 21.

FIG. 3 is a graph showing in vitro release of DOX-loaded HA-Lys-LA crosslinked nanoparticles triggered by glutathione. As shown by the results, the DOX-loaded crosslinked nanoparticles were rapidly decrosslinked in 10 mM GSH at 37° C. and about 86% DOX was released in 22 h; while DOX-loaded crosslinked nanoparticles were very stable in an environment free of GSH, and a little DOX was released, only 24%.

Example 22 Loading of Small Molecular Anticancer Drug Doxorubicin and Its Glutathione-Triggered Release A solution of HA-Lys-LA ($M_{nHA}$=35 kDa, DS=40%)/formamide (5 mg/mL, 1 mL) was mixed with doxorubicin (DOX)/dimethylsulfoxide (5 mg/mL, 0.25 mL) under stirring for 1 h, and 4 ml of PBS was added dropwise to the mixture under stirring at 25° C. After being stirred for 1 h, the resulting solution was loaded into a previously prepared dialysis bag (SPECTRA/POR, MWCO: 3500) and dialyzed against PBS, to form a solution of drug-loaded polymer nanoparticles.

The formed drug-loaded polymer nanoparticle solution was taken in half volume and was adjusted to pH 8.5. 17.5 mL, of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The crosslinked drug-loaded nanoparticles were dialyzed against PBS to remove the unreacted DTT.

The DOX-loaded crosslinked nanoparticles were 100-fold diluted with PBS (10 mM, pH 7.4) and divided into two portions: an equal volume of PBS of GSH (10 mM) was added to one portion, and an equal volume of pure PBS was added to the other portion at 37° C. These solutions were immediately transferred to a dialysis bag and placed in a 37° C. thermostat shaker (200 rpm). The former was immersed in 25 mL of PBS having the same GSH concentration at the same temperature, and the latter was immersed in 25 mL of PBS (20 mM) at the same temperature; after a given time period, 6 mL of dialysate outside the dialysis bag was taken to determine its fluorescence intensity, and 6 mL of a corresponding fresh solution was added to the outside of the dialysis bag.

Determination of drug loading efficiency of DOX in polymer nanoparticles: a certain amount of crosslinked and uncrosslinked drug-loaded nanoparticles solutions were taken, and the water in the solution was removed by a freeze-drying method; then 0.5 mL of formamide was added thereto, and the freeze-dried solid was fully fused with ultrasound for 1 h; 20 ml of the resulting solution was taken, to which 3 ml of formamide was added; after fluorescence test, the drug loading efficiency and drug loading content were calculated with reference to a standard curve of doxorubicin.

Drug loading efficiency=(weight of loaded doxorubicin in nanoparticles/weight of doxorubicin in feed)×100%

Drug loading content=(weight of loaded doxorubicin in nanoparticles/total weight of the blank nanoparticles and doxorubicin in feed)×100%

When the theoretical drug loading content is 25%, the drug loading efficiency of HA-lys-LA$_{40}$ crosslinked nanoparticles to doxorubicin was 74.5%, and the actual drug loading content was 20%.

The DOX-loaded crosslinked nanoparticles were rapidly decrosslinked in 10 mM GSH at 37° C. and about 78% DOX was released in 22 h; while DOX-loaded crosslinked nanoparticles were very stable in an environment free of GSH, and a little DOX was released, only 19%.

Example 23 Loading of Small Molecular Anticancer Drug Paclitaxel (PTX) and its DTT-Triggered Release A solution of HA-Lys-LA (M$_{nHA}$=35 kDa, DS=10%)/formamide (5 mg/mL, 1 mL) was mixed with PTX/N,N'-dimethylformamide (5 mg/mL, 0.25 mL) under stirring for 1 h, and 4 ml of PBS was added dropwise to the mixture under stirring at 25° C. After being stirred for 1 h, the resulting solution was loaded into a previously prepared dialysis bag (SPECTRA/POR, MWCO: 3500) and dialyzed against PBS, to form a solution of drug-loaded polymer nanoparticles.

The formed drug-loaded polymer nanoparticle solution was taken in half volume and was adjusted to pH 8.5. 17.5 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The crosslinked drug-loaded nanoparticles were dialyzed against PBS to remove the unreacted DTT.

The PTX-loaded crosslinked NPs (nanoparticles) were 100-fold diluted with PBS (10 mM, pH 7.4) and divided into two portions: an equal volume of PBS of DTT (10 mM) was added to one portion, and an equal volume of pure PBS was added to the other portion at 37° C. These solutions were immediately transferred to a dialysis bag and placed in a 37° C. thermostat shaker (200 rpm). The former was immersed in 25 mL of PBS having the same DTT concentration at the same temperature, and the latter was immersed in 25 mL of PBS (10 mM) at the same temperature; after a given time period, 6 mL of dialysate outside the dialysis bag was taken to determine its fluorescence intensity, and 6 mL of a corresponding fresh solution was added to the outside of the dialysis bag.

Determination of drug loading efficiency of PTX in polymer nanoparticles: a certain amount of crosslinked and uncrosslinked drug-loaded nanoparticles solutions were taken, and the water in the solution was removed by a freeze-drying method; then 0.5 mL of acetonitrile was added thereto to perform ultrasound for 1 h; filtration was performed; the adsorption intensity at 227 nm was measured by high performance liquid chromatography (HPLC) with a mixture of acetonitrile and water (1/1, v/v) as the mobile phase, and the drug loading efficiency was calculated with reference to the standard curve of paclitaxel.

Drug loading efficiency=(mass of paclitaxel in nanoparticles/mass of paclitaxel in feed)×100%

Drug loading content=(mass of paclitaxel in nanoparticles/total mass of the nanoparticles and paclitaxel in feed)×100%

As shown by the results, PTX did not affect the formation of nanoparticles and the size substantially did not change; besides, when the theoretical drug loading content is 30%, the drug loading efficiency of HA-lys-LA$_{10}$ crosslinked nanoparticles to paclitaxel was 67.2%, and the actual drug loading content was 22%. The PTX-loaded crosslinked nanoparticles were rapidly decrosslinked in 10 mM DTT at 37° C. and about 82% PTX was released in 22 h.

Example 24 A Method of Synthesizing a Polymer HA-(Aminoethylamino)-LA (M$_{nHA}$=8.9 kDa, DS=5%)

Firstly, triethylamine (42.5 mg, 0.42 mmol) was added to a solution of NH$_2$—CH$_2$CH$_2$NH(Boc).HCl (64.08 mg, 0.40 mmol)/anhydrous methanol (2 mL) at room temperature. The mixture was stirred for 1 h. EDC (460 mg, 2.40 mmol), NHS (140 mg, 1.22 mmol) and hydrochloride-removed NH$_2$—CH$_2$CH$_2$NH(Boc)/methanol solution were added in order to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-NHCH$_2$CH$_2$NH-Boc. Totally 6 mL of trifluoroacetic acid/2M hydrochloric acid (v/v 1:1) were added in order to the obtained solid HA-NHCH$_2$CH$_2$NH-Boc. The reaction was carried out with stirring for 6 h. After the deprotection finished, the solution was adjusted to pH 7.0, followed by dialysis and lyophilization, to give HA-NHCH$_2$CH$_2$NH$_2$.

Lipoic acid (6 mg, 29 μmol) was dissolved in 2.0 mL of dichloromethane and added to a 13 mL Schlenk vacuum sealed flask, and DCC (0.192 g, 0.93 mmol) dissolved in 0.5 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-NHCH$_2$CH$_2$NH$_2$ (114.4 mg, 15 µmol amino) dissolved in 5 mL formamide, the lipoic acid anhydride, and 4-dimethylaminopyridine (2 mg, 16.5 µmol) dissolved in 0.5 mL of N,N'-dimethylformamide were added in order to a 50 mL three-necked flask under a nitrogen atmosphere; the reactor was placed in an 30° C. oil bath and stirred for 48 h, followed by dialysis in water/ethanol (1/1) and water in order, and lyophilized. Yield: 97%. The results of NMR showed that the structure was HA-(aminoethylamino)-LA, in which the degree of substitution (DS) of aminoethylamino-lipoyl was 5%.

Example 25 A Method of Synthesizing a Polymer HA-(Aminoethylamino)-LA (M$_{nHA}$=100 kDa, DS=10%)

Firstly, triethylamine (85 mg, 0.84 mmol) was added to a solution of NH$_2$—CH$_2$CH$_2$NH(Boc)-HCl. (128.2 mg. 0.80 mmol)/anhydrous methanol (2 mL) at room temperature. The mixture was stirred for 1 h. EDC (460 mg, 2.40 mmol), NHS (140 mg, 1.22 mmol) and hydrochloride-removed NH$_2$—CH$_2$CH$_2$NH(Boc)/methanol solution were added in order to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-NHCH$_2$CH$_2$NH-Boc. Totally 6 mL of trifluoroacetic acid/2M hydrochloric acid (v/v 1:1) were added in order to the obtained solid HA-NHCH$_2$CH$_2$NH-Boc. The reaction was carried out with stirring for 6 h. After the deprotection finished, the solution was adjusted to pH 7.0, followed by dialysis and lyophilization. Yield: 92%. The results of NMR showed that the structure was HA-NHCH$_2$CH$_2$NH$_2$, in which the degree of substitution (DS) of aminoethylamino was 10%.

Lipoic acid (12 mg, 58 mol) was dissolved in 2.0 mL of dichloromethane and added to a 25 mL Schlenk vacuum sealed flask, and DCC (6 mg, 29 µmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-NHCH$_2$CH$_2$NH$_2$ (103.6 mg, 27 µmol amino) dissolved in 5 mL formamide, the lipoic acid anhydride, and 4-dimethylaminopyridine (4 mg, 33 µmol) dissolved in 0.5 mL of N,N'-dimethylformamide were added in order to a 50 mL three-necked flask under a nitrogen atmosphere; the reactor was placed in an 30° C. oil bath and stirred for 48 h, followed, by dialysis in water/ethanol (1/1) and water in order, and lyophilized. The results of NMR showed that the structure was HA-(aminoethylamino)-LA, in which the degree of substitution (DS) of aminoethyl-amino-lipoyl was 10%.

Example 26 A Method of Synthesizing a Polymer HA-(Aminoethylamino)-LA (M$_{nHA}$=37 kDa, DS=28%)

Firstly, triethylamine (167.9 mg, 1.66 mmol) was added to a solution of NH$_2$—CH$_2$CH$_2$NH(Boc).HCl (310.7 mg, 1.58 mmol)/anhydrous methanol (2 mL) at room temperature. The mixture was stirred for 1 h. EDC (460 mg, 2.40 mmol), NHS (140 mg, 1.22 mmol) and hydrochloride-removed NH$_2$—CH$_2$CH$_2$NH(Boc)/methanol solution were added in order to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-NHCH$_2$CH$_2$NH-Boc. Totally 6 mL of trifluoroacetic acid/2M hydrochloric acid (v/v 1:1) were added in order to the obtained solid HA-NHCH$_2$CH$_2$NH-Boc. The reaction was carried out with stirring for 6 h. After the deprotection finished, the solution was adjusted to pH 7.0, followed by dialysis and lyophilization. Yield: 92%. The results of NMR showed that the structure was HA-NHCH$_2$CH$_2$NH$_2$, in which the degree of substitution (DS) of aminoethylamino was 28%.

Lipoic acid (32 mg, 152 µmol) was dissolved in 2.0 mL of dichloromethane and added to a 25 mL Schlenk vacuum sealed flask, and DCC (16 mg, 76 µmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HANH—CH$_2$CH$_2$NH$_2$ (106 mg, 76 µmol amino) dissolved in 5 mL formamide, the lipoic acid anhydride, and 4-dimethylaminopyridine (10 mg, 83 µmol) dissolved in 0.5 mL of N,N'-dimethylformamide were added in order to a 50 mL three-necked flask under a nitrogen atmosphere; the reactor was placed in an 30° C. oil bath and stirred for 48 h, followed by dialysis in water/ethanol (1/1) and water in order, and lyophilized. The results of NMR showed that the structure was A-(aminoethylamino)-LA, in which the degree of substitution (DS) of aminoethylamino-lipoyl was 28%.

Example 27 A Method of Synthesizing a Polymer HA-(Aminohexylamino)-LA (M$_{nHA}$=400 kDa, DS=40%)

Firstly, triethylamine (167.9 mg, 1.66 mmol) was added to a solution of NH$_2$—(CH$_2$CH$_2$)$_3$NH(Boc).HCl (310.7 mg, 1.58 mmol)/anhydrous methanol (2 mL) at room temperature. The mixture was stirred for 1 h. EDC (460 mg, 2.40 mmol), NHS (140 mg, 1.22 mmol) and hydrochloride-removed NH$_2$—CH$_2$CH$_2$NH(Boc)/methanol solution were added in order to an aqueous solution of HA (300 mg, 0.79 mmol carboxyl group) (6 mL). The solution was adjusted to pH 8.5. The mixture was stirred for 96 h at room temperature, followed by dialysis and lyophilization, to obtain HA-NH(CH$_2$CH$_2$)$_3$NH-Boc. Totally 6 mL of trifluoroacetic acid/2M hydrochloric acid (v/v 1:1) were added in order to the obtained solid HA-NH(CH$_2$CH$_2$)$_3$NH-Boc. The reaction was carried out with stirring for 6 h. After the deprotection finished, the solution was adjusted to pH 7.0, followed by dialysis and lyophilization. Yield: 89%. The results of NMR showed that the structure was HA-NH(CH$_2$CH$_2$)$_3$NH$_2$, in which the degree of substitution (DS) of aminohexylamino was 40%.

Lipoic acid (32 mg, 152 µmol) was dissolved in 2.0 mL of dichloromethane and added to a 25 mL Schlenk vacuum sealed flask, and DCC (16 mg, 76 µmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-NH(CH$_2$CH$_2$)$_3$NH$_2$ (79 mg, 76 µmol amino) dissolved in 5 mL formamide, the lipoic acid anhydride, and 4-dimethylaminopyridine (10 mg, 83 µmol) dissolved in 0.5 mL of N,N'-dimethylformamide were added in order to a 50 mL three-necked flask under a nitrogen atmosphere; the reactor was placed in an 30° C. oil bath and stirred for 48 h, followed by dialysis in water/ethanol (1/1) and water in order, and lyophilized. The results of NMR showed that the structure was HA-(aminohexylamino)-LA, in which the degree of substitution (DS) of aminohexylamino-lipoyl was 40%.

Example 28 A Method of Synthesizing a Polymer HA-Ornithine-LA ($M_{nHA}$=8.91 kDa, DS=10%)

Firstly, triethylamine (85 mg, 0.84 mmol) was added to a solution of Orn(Boc).HCl (215 mg, 0.80 mmol)/anhydrous methanol (2 mL) at room temperature. The mixture was stirred for 1 h. EDC (460 mg, 2.40 mmol), NHS (140 mg, 1.22 mmol) and hydrochloride-removed Orn(Boc)/methanol solution were added in order to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-Orn(Boc). Totally 6 mL of trifluoroacetic acid/2M hydrochloric acid (v/v 1:1) were added in order to the obtained solid HA-Orn(Boc). The reaction was carried out with stirring for 6 h, After the deprotection finished, the solution was adjusted to pH 7.0, followed by dialysis and lyophilization. Yield: 92%. The results of NMR showed that the structure was HA-Orn, in which the degree of substitution (DS) of ornithine (Orn) was 10%.

Lipoic acid (12 mg, 58 µmol) was dissolved in 2.0 mL of dichloromethane and added to a 25 mL Schlenk vacuum sealed flask, and DCC (6 mg, 29 µmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Orn (105.2 mg, 27 µmol amino) dissolved in 5 mL formamide, the lipoic acid anhydride, and 4-dimethylaminopyridine (4 mg, 33 µmol) dissolved in 0.5 mL of N,N'-dimethylformamide were added in order to a 50 mL three-necked flask under a nitrogen atmosphere; the reactor was placed in an 30° C. oil bath and stirred for 48 h, followed by dialysis in water/ethanol (1/1) and water in order, and lyophilized. The results of NMR showed that the structure was HA-Orn-LA, in which the degree of substitution (DS) of ornithine-lipoyl was 10%.

Example 29 A Method of Synthesizing a Polymer HA-Ornithine-LA ($M_{nHA}$=8.9 kDa, DS=28%)

Firstly, triethylamine (167.9 mg, 1.66 mmol) was added to a solution of Orn(Boc).HCl (424.6 mg, 1.58 mmol)/anhydrous methanol (2 mL) at room temperature. The mixture was stirred for 1 h. EDC (460 mg, 2.40 mmol), NHS (140 mg, 1.22 mmol) and hydrochloride-removed Orn(Boc)/methanol solution were added in order to an aqueous solution of FIA (300 mg, 0.79 mmol carboxyl group) (6 mL). The solution was adjusted to pH 8.5. The mixture was stirred for 24 h at room temperature, followed by dialysis and lyophilization, to obtain HA-Orn(Boc). Totally 6 mL of trifluoroacetic acid/2M hydrochloric acid (v/v 1:1) were added in order to the obtained solid HA-Orn(Boc). The reaction was carried out with stirring for 6 h. After the deprotection finished, the solution was adjusted to pH 7.0, followed by dialysis and lyophilization. Yield: 92%. The results of NMR showed that the structure was HA-Orn, in which the degree of substitution (DS) of ornithine (Orn) was 28%.

Lipoic acid (32 mg, 152 µmol) was dissolved in 2.0 mL of dichloromethane and added to a 25 mL Schlenk vacuum sealed flask, and DCC (16 mg, 76 µmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Orn (110.7 mg, 76 µmol amino) dissolved in 5 mL formamide, the lipoic acid anhydride, and 4-dimethylaminopyridine (10 mg, 83 µmol) dissolved in 0.5 mL of N,N'-dimethylformamide were added in order to a 50 mL three-necked flask under a nitrogen atmosphere; the reactor was placed in an 30° C. oil bath and stirred for 48 h, followed by dialysis in water/ethanol (1/1) and water in order, and lyophilized. The results of NMR showed that the structure was HA-Orn-LA, in which the degree of substitution (DS) of ornithine-lipoyl was 28%.

Example 30 A Method of Synthesizing a Polymer HA-Ornithine-LA ($M_{nHA}$=100 kDa, DS=28%)

Firstly, triethylamine (167.9 mg, 1.66 mmol) was added to a solution of Orn(Boc).HCl (424.6 mg, 1.58 mmol)/anhydrous methanol (2 mL) at room temperature. The mixture was stirred for 1 h. EDC (460 mg, 2.40 mmol), NHS (140 mg, 1.22 mmol) and hydrochloride-removed Orn(Boc)/methanol solution were added in order to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-Orn(Boc). Totally 6 mL of trifluoroacetic acid/2M hydrochloric acid (v/v 1:1) were added in order to the obtained solid HA-Orn(Boc). The reaction was carried out with stirring for 6 h. After the deprotection finished, the solution was adjusted to pH 7.0, followed by dialysis and lyophilization. Yield: 92%. The results of NMR showed that the structure was HA-Orn, in which the degree of substitution (DS) of ornithine (Orn) was 28%.

Lipoic acid (32 mg, 152 µmol) was dissolved in 2.0 mL of dichloromethane and added to a 25 mL Schlenk vacuum sealed flask, and DCC (16 mg, 76 µmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Orn (110.7 mg, 76 μmol amino) dissolved in 5 mL formamide, the lipoic acid anhydride, and 4-dimethylaminopyridine (10 mg, 83 μmol) dissolved in 0.5 mL of N,N'-dimethylformamide were added in order to a 50 mL three-necked flask under a nitrogen atmosphere; the reactor was placed in an 30° C. oil bath and stirred for 48 h, followed by dialysis in water/ethanol (1/1) and water in order, and lyophilized. The results of NMR showed that the structure was HA-Orn-LA, in which the degree of substitution (DS) of ornithine-lipoyl was 28%.

Example 31 A Method of Synthesizing a Polymer HA-Ornithine-LA ($M_{nHA}$=300 kDa, DS=40%)

Firstly, triethylamine (167.9 mg, 1.66 mmol) was added to a solution of Orn(Boc).HCl (424.6 mg, 1.58 mmol)/anhydrous methanol (2 mL) at room temperature. The mixture was stirred for 1 h. EDC (460 mg, 2.40 mmol), NHS (140 mg, 1.22 mmol) and hydrochloride-removed Orn(Boc)/methanol solution were added in order to an aqueous solution of HA (300 mg, 0.79 mmol carboxyl group) (6 mL). The solution was adjusted to pH 8.5, The mixture was stirred for 96 h at room temperature, followed by dialysis and lyophilization, to obtain HA-Orn(Boc). Totally 6 mL of trifluoroacetic acid/2M hydrochloric acid (v/v 1:1) were added in order to the obtained solid HA-Orn(Boc). The reaction was carried out with stirring for 6 h. After the deprotection finished, the solution was adjusted to pH 7.0, followed by dialysis and lyophilization. Yield: 89%. The results of NMR showed that the structure was HA-Orn, in which the degree of substitution (DS) of ornithine (Orn) was 40%.

Lipoic acid (32 mg, 152 μmol) was dissolved in 2.0 mL of dichloromethane and added to a 25 mL Schlenk vacuum sealed flask, and DCC (16 mg, 76 μmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Orn (79.8 mg, 76 μmol amino) dissolved in 5 mL formamide, the lipoic acid anhydride, and 4-dimethylaminopyridine (10 mg, 83 μmol) dissolved in 0.5 mL of N,N'-dimethylformamide were added in order to a 50 mL three-necked flask under a nitrogen atmosphere; the reactor was placed in an 30° C. oil bath and stirred for 48 h, followed by dialysis in water/ethanol (1/1) and water in order, and lyophilized. The results of NMR showed that the structure was HA-Orn-LA, in which the degree of substitution (DS) of ornithine-lipoyl was 40%.

Example 32 A Method of Synthesizing a Polymer HA-Ornithine Ethyl Ester-LA ($M_{nHA}$=8.9 kDa, DS=5%)

Firstly, triethylamine (42.5 mg, 0.42 mmol) was added to a solution of Orn(Boc)-OEt.HCl (107.5 mg, 0.40 mmol)/anhydrous methanol (2 mL) at room temperature. The mixture was stirred for 1 h. EDC (460 mg, 2.40 mmol), NHS (140 mg, 1.22 mmol) and hydrochloride-removed Orn(Boc)-OEt/methanol solution were added in order to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-Orn(Boc)-OEt. Totally 6 mL of trifluoroacetic acid/2M hydrochloric acid (v/v 1:1) were added in order to the obtained solid HA-Orn (Boc)-OEt. The reaction was carried out with stirring for 6 h. After the deprotection finished, the solution was adjusted to pH 7.0, followed by dialysis and lyophilization, to give HA-Orn(OEt).

Lipoic acid (6 mg, 29 μmol) was dissolved in 2.0 mL of dichloromethane and added to a 13 mL Schlenk vacuum sealed flask, and DCC (0.192 g, 0.93 mmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Orn(OEt) (115.5 mg, 15 μmol amino) dissolved in 5 mL formamide, the lipoic acid anhydride, and 4-dimethylaminopyridine (2 mg, 16.5 μmol) dissolved in 0.5 mL of N,N'-dimethylformamide were added in order to a 50 mL three-necked flask under a nitrogen atmosphere; the reactor was placed in an 30° C. oil bath and stirred for 48 h, followed by dialysis in water/ethanol (1/1) and water in order, and lyophilized. Yield: 97%. The results of NMR showed that the structure was HA-Orn(OEt)-LA, in which the degree of substitution (DS) of ornithine(OEt)-lipoyl was 5%.

Example 33 A Method of Synthesizing a Polymer HA-Ornithine Methyl Ester-LA ($M_{nHA}$=35 kDa, DS=28%)

Firstly, triethylamine (167.9 mg, 1.66 mmol) was added to a solution of Orn(Boc)-OMe.HCl (402.5 mg, 1.58 mmol)/anhydrous methanol (2 mL) at room temperature. The mixture was stirred for 1 h. EDC (460 mg, 2.40 mmol), NHS (140 mg, 1.22 mmol) and hydrochloride-removed Orn (Boc)-OMe/methanol solution were added in order to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-Orn(Boc)-OMe. Totally 6 mL of trifluoroacetic acid/2M hydrochloric acid (v/v 1:1) were added in order to the obtained solid HA-Orn(Boc)-OMe. The reaction was carried out with stirring for 6 h. After the deprotection finished, the solution was adjusted to pH 7.0, followed by dialysis and lyophilization. Yield: 92%. The results of NMR showed that the structure was HA-Orn(OMe), in which the degree of substitution (DS) of Orn(OMe) was 28%.

Lipoic acid (32 mg, 152 μmol) was dissolved in 2.0 mL of dichloromethane and added to a 25 mL Schlenk vacuum sealed flask, and DCC (16 mg, 76 μmol) dissolved in 1.0 mL of dichloromethane was added to the sealed flask under a nitrogen atmosphere; the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Orn(OMe) (110.6 mg, 76 μmol amino) dissolved in 5 mL formamide, the lipoic acid anhydride, and 4-dimethylaminopyridine (10 mg, 83 µmol) dissolved in 0.5 mL of N,N'-dimethylformamide were added to a 50 mL three-necked flask under a nitrogen atmosphere; the reactor was placed in an 30° C. oil bath and stirred for 48 h, followed by dialysis in water/ethanol (1/1) and water in order, and lyophilized. The results of NMR showed that the structure was HA-Orn(OMe)-LA, in which the degree of substitution (DS) of ornithine(OMe)-lipoyl was 28%.

Example 34 A Method of Synthesizing a Polymer HA-Ornithine Butyl Ester-LA ($M_{nHA}$=500 kDa, DS=28%)

Firstly, triethylamine (167.9 mg, 1.66 mmol) was added to a solution of Orn(Boc)-OBu HCl (469.0 mg, 1.58 mmol)/anhydrous methanol (2 mL) at room temperature. The mixture was stirred for 1 h. EDC (460 mg, 2.40 mmol), NHS (140 mg, 1.22 mmol) and hydrochloride-removed Orn(Boc)-OBu/methanol solution were added in order to an aqueous solution of HA (300 mg, 0.79 mmol carboxyl group) (6 mL). The solution was adjusted to pH 8.5. The mixture was stirred for 24 h at room temperature, followed by dialysis and lyophilization, to obtain HA-Orn(Boc)-OBu. Totally 6 mL of trifluoroacetic acid/2M hydrochloric acid (v/v 1:1) were added in order to the obtained solid HA-Orn(Boc)-OBu. The reaction was carried out with stirring for 6 h. After the deprotection finished, the solution was adjusted to pH 7.0, followed by dialysis and lyophilization. Yield: 92%. The results of NMR showed that the structure was HA-Orn(OBu), in which the degree of substitution (DS) of Orn(OBu) was 28%.

Lipoic acid (32 mg, 152 µmol) was dissolved in 2.0 mL of dichloromethane and added to a 25 mL Schlenk vacuum sealed flask, and DCC (16 mg, 76 µmol) dissolved in 1.0 mL of dichloromethane was added to the sealed flask under a nitrogen atmosphere, the flask was placed in a 30° C. oil bath and stirred for 22 h. After cooling, the urea formed in the reaction was removed by filtration. The filtrate was concentrated via rotary evaporation and the solvent was removed, to give a lipoic acid anhydride.

The lipoic acid anhydride obtained above was dissolved in 0.5 mL of N,N'-dimethylformamide having undergone anhydrous treatment. HA-Orn(OBu) (113.8 mg, 76 µmol amino) dissolved in 5 mL formamide, the lipoic acid anhydride, and 4-dimethylaminopyridine (10 mg, 83 µmol) dissolved in 0.5 mL of N,N'-dimethylformamide were added to a 50 mL three-necked flask under a nitrogen atmosphere; the reactor was placed in an 30° C. oil bath and stirred for 48 h, followed by dialysis in water/ethanol (1/1) and water in order, and lyophilized. The results of NMR showed that the structure was HA-Orn(OBu)-LA, in which the degree of substitution (DS) of ornithine(OBu)-lipoyl was 28%.

Example 35 Preparation of HA-(Aminoethylamino)-LA ($M_{nHA}$=37 kDa, DS=28%) Nanoparticles HA-(aminoethylamino)-LA ($M_{nHA}$=37 kDa, DS=28%) nanoparticles were prepared according to the method in Example 9. The average particle size of the nanoparticles was 132 nm and the particle size distribution was 0.08.

Example 36 Preparation of HA-(Aminohexylamino)-LA ($M_{nHA}$=400 kDa, DS=40%) Nanopartieles HA-(aminohexylamino)-LA ($M_{nHA}$=400 kDa, DS=40%) nanoparticles were prepared according to the method in Example 9. The average particle size of the nanoparticles was 145 nm and the particle size distribution was 0.11.

Example 37 Preparation of HA-Ornithine-LA ($M_{nHA}$=100 kDa, DS=28%) Nanoparticles HA-ornithine-LA ($M_{nHA}$=100 kDa, DS=28%) nanoparticles were prepared to the method in Example 9. The average particle size of the nanoparticles was 140 nm and the particle size distribution was 0.07.

Example 38 Preparation of HA-Ornithine(OMe)-LA ($M_{nHA}$=35 kDa, DS=28%) Nanoparticles HA-ornithine(OMe)-LA ($M_{nHA}$=35 kDa, DS=28%) nanoparticles were prepared according to the method in Example 9. The average particle size of the nanoparticles was 148 nm and the particle size distribution was 0.06.

Example 39 Preparation of HA-Ornithine(OBu)-LA ($M_{nHA}$=500 kDa, DS=28%) Nanoparticles HA-ornithine(OBu)-LA ($M_{nHA}$=500 kDa, DS=28%) nanoparticles were prepared according to the method in Example 9. The average particle size of the nanoparticles was 151 nm and the particle size distribution was 0.12.

Example 40 Crosslinking of HA-(Aminoethylamino)-LA ($M_{nHA}$=37 kDa, DS=28%) Nanoparticles In order to obtain crosslinked polymer nanoparticles, a solution of the above-formed polymer nanoparticles (0.5 mg/ml, 2 ml) was adjusted to pH 8.5, 20 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted DTT. The crosslinked nanoparticles had a size of 150 nm and a particle size distribution of 0.13, and had significant stability against high dilution (simulated intravenous injection) and high salinity (2M).

Example 41 Crosslinking of HA-(Aminohexylamino)-LA ($M_{nHA}$=400 kDa, DS=40%) Nanoparticles In order to obtain crosslinked polymer nanoparticles, a solution of the above-formed polymer nanoparticles (0.5 mg/ml, 2 ml) was adjusted to pH 8.5, 20 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted DTT. The crosslinked nanoparticles had a size of 149 nm and a particle size distribution of 0.13, and had significant stability against high dilution (simulated intravenous injection) and high salinity (2M).

Example 42 Crosslinking of HA-Ornithine-LA ($M_{nHA}$=100 kDa, DS=28%) Nanoparticles In order to obtain crosslinked polymer nanoparticles, a solution of the above-formed polymer nanoparticles (0.5 mg/ml, 2 ml) was adjusted to pH 8.5, 20 mL of 1 mg/mL 1, 4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted DTT. The crosslinked nanoparticles had a size of 137 nm and a particle size distribution of 0.08, and had significant stability against high dilution (simulated intravenous injection) and high salinity (2M).

Example 43 Crosslinking of HA-Ornithine(OMe)-LA ($M_{nHA}$=35 kDa, DS=28%) Nanoparticles In order to obtain crosslinked polymer nanoparticles, a solution of the above-formed polymer nanoparticles (0.5 mg/ml, 2 ml) was adjusted to pH 8.5, 20 mL of 1 mg/mL1,4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted DTT. The crosslinked nanoparticles had a size of 132 nm and a particle size distribution of 0.09, and had significant stability against high dilution (simulated intravenous injection) and high salinity (2M).

Example 44 Crosslinking of HA-Ornithine(OBu)-LA ($M_{nHA}$=500 kDa, DS=28%) Nanoparticles In order to obtain crosslinked polymer nanoparticles, a solution of the above-formed polymer nanoparticles (0.5 mg/ml, 2 ml) was adjusted to pH 8.5, 20 mL of 1 mg/mL1,4-dithio-D,L-threobutanol (DTT) was added thereto after inletting of nitrogen gas for 10 minutes; the mixed solution was stirred for 24 h to undergo reaction at room temperature under nitrogen atmosphere. The resulting crosslinked nanoparticles were dialyzed against PBS to remove the unreacted DTT. The crosslinked nanoparticles had a size of 141 nm and a particle size distribution of 0.14, and had significant stability against high dilution (simulated intravenous injection) and high salinity (2M).

Example 45 Loading of Small Molecular Anticancer Drug Doxorubicin (DOX) and Its Glutathione-Triggered Release A solution of HA-ornithine(OMe)-LA ($M_{nHA}$=35 kDa, DS=28%, 10%)/formamide (5 mg/mL, 1 mL) was mixed with doxorubicin (DOX)/dimethylsulfoxide (5 mg/mL, 0.25 mL) under stirring for 1 h, and 4 ml of PBS was added dropwise to the mixture under stirring at 25° C. After being stirred for 1 h, the resulting solution was loaded into a previously prepared dialysis bag (SPECTRA/POR, MWCO: 3500) and dialyzed against PBS, to form a solution of drug-loaded polymer nanoparticles.

The formed drug-loaded polymer nanoparticle solution was taken in half volume and was adjusted to pH 8.5. 17.5 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The crosslinked drug-loaded nanoparticles were dialyzed against PBS to remove the unreacted DTT.

The DOX-loaded crosslinked nanoparticles were 100-fold diluted with PBS (10 mM, pH 7.4) and divided into two portions: an equal volume of PBS of GSH (10 mM) was added to one portion, and an equal volume of pure PBS was added to the other portion at 37° C. These solutions were immediately transferred to a dialysis bag and placed in a 37° C. thermostat shaker (200 rpm). The former was immersed in 25 mL of PBS having the same GSH concentration at the same temperature, and the latter was immersed in 25 mL of PBS (20 mM) at the same temperature; after a given time period, 6 mL of dialysate outside the dialysis bag was taken to determine its fluorescence intensity, and 6 mL of a corresponding fresh solution was added to the outside of the dialysis bag.

Determination of drug loading efficiency of DOX in polymer nanoparticles: a certain amount of crosslinked and uncrosslinked drug-loaded nanoparticles solutions were taken, and the water in the solution was removed by a freeze-drying method; then 0.5 mL of formamide was added thereto, and the freeze-dried solid was fully fused with ultrasound for 1 h; 20 ml of the resulting solution was taken, to which 3 ml of formamide was added; after fluorescence test, the drug loading efficiency and drug loading content were calculated with reference to a standard curve of doxorubicin.

Drug loading efficiency=(weight of loaded doxorubicin in nanoparticles/weight of doxorubicin in feed)×100%

Drug loading content=(weight of loaded doxorubicin in nanoparticles/total weight of the blank nanoparticles and doxorubicin in feed)×100%

When the theoretical drug loading content is 20%, the drug loading efficiency of HA-ornithine(OMe)-LA ($M_{nHA}$=35 kDa, DS=10%) crosslinked nanoparticles to doxorubicin was 79.57%, and the actual drug loading content was 15.56%.

When the theoretical drug loading content is 20%, the drug loading efficiency of HA-ornithine(OMe)-LA ($M_{nHA}$=35 kDa, DS=28%) crosslinked nanoparticles to doxorubicin was 81.2%, and the actual drug loading content was 16.24%.

The DOX-loaded crosslinked nanoparticles were rapidly decrosslinked in 10 mM GSH at 37° C. and about 81% DOX was released in 22 h; while DOX-loaded crosslinked nanoparticles were very stable in an environment free of GSH, and a little DOX was released, only 16%.

Example 46 Loading of Small Molecular Anticancer Drug Doxorubicin (DOX) and Its Glutathione-Triggered Release A solution of HA-ornithine-LA ($M_{nHA}$=35 kDa, DS=10%)/formamide (5 mg/mL, 1 mL) was mixed with doxorubicin (DOX)/dimethylsulfoxide (5 mg/mL, 0.25 mL) under stirring for 1 h, and 4 ml of PBS was added dropwise to the mixture under stirring at 25° C. After being stirred for 1 h, the resulting solution was loaded into a previously prepared dialysis bag (SPECTRA/POR, MWCO: 3500) and dialyzed against PBS, to form a solution of drug-loaded polymer nanoparticles.

The formed drug-loaded polymer nanoparticle solution was taken in half volume and was adjusted to pH 8.5. 17.5 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The crosslinked drug-loaded nanoparticles were dialyzed against PBS to remove the unreacted DTT.

The DOX-loaded crosslinked nanoparticles were 100-fold diluted with PBS (10 mM, pH 7.4) and divided into two portions: an equal volume of PBS of GSH (10 mM) was added to one portion, and an equal volume of pure PBS was added to the other portion at 37° C. These solutions were immediately transferred to a dialysis bag and placed in a 37° C. thermostat shaker (200 rpm).) The former was immersed in 25 mL of PBS having the same GSH concentration at the same temperature, and the latter was immersed in 25 mL of PBS (20 mM) at the same temperature; after a given time period, 6 mL of dialysate outside the dialysis bag was taken to determine its fluorescence intensity, and 6 mL of a corresponding fresh solution was added to the outside of the dialysis bag.

Determination of drug loading efficiency of DOX in polymer nanoparticles: a certain amount of crosslinked and uncrosslinked drug-loaded nanoparticles solutions were taken, and the water in the solution was removed by a freeze-drying method; then 0.5 mL of formamide was added thereto, and the freeze-dried solid was fully fused with ultrasound for 1 h; 20 ml of the resulting solution was taken, to which 3 ml of formamide was added; after fluorescence test, the drug loading efficiency and drug loading content were calculated with reference to a standard curve of doxorubicin.

Drug loading efficiency=(weight of loaded doxorubicin in nanoparticles/weight of doxorubicin in feed)×100%

Drug loading content=(weight of loaded doxorubicin in nanoparticles/total weight of the blank nanoparticles and doxorubicin in feed)×100%

When the theoretical drug loading content is 20%, the drug loading efficiency of HA-ornithine-LA ($M_{nHA}$=35 kDa, DS=10%) crosslinked nanoparticles to doxorubicin was 81.5%, and the actual drug loading content was 16.38%.

The DOX-loaded crosslinked nanoparticles were rapidly decrosslinked in 10 mM GSH at 37° C. and about 82% DOX was released in 22 h; while DOX-loaded crosslinked nanoparticles were very stable in an environment free of GSH, and a little DOX was released, only 15%.

Example 47 Loading of Small Molecular Anticancer Drug Doxorubicin and Its Glutathione-Triggered Release A solution of HA-(aminohexylamino)-LA ($M_{nHA}$=400 kDa, DS=40%)/formamide (5 mg/mL, 1 mL) was mixed with doxorubicin (DOX)/dimethylsulfoxide (5 mg/mL, 0.25 mL) under stirring for 1 h, and 4 ml of PBS was added dropwise to the mixture under stirring at 25° C., After being stirred for 1 h, the resulting solution was loaded into a previously prepared dialysis bag (SPECTRA/POR, MWCO: 3500) and dialyzed against PBS, to form a solution of drug-loaded polymer nanoparticles.

The formed drug-loaded polymer nanoparticle solution was taken in half volume and was adjusted to pH 8.5. 17.5 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The crosslinked drug-loaded nanoparticles were dialyzed against PBS to remove the unreacted DTT.

The DOX-loaded crosslinked nanoparticles were 100-fold diluted with PBS (10 mM, pH 7.4) and divided into two portions: an equal volume of PBS of GSH (10 mM) was added to one portion, and an equal volume of pure PBS was added to the other portion at 37° C. These solutions were immediately transferred to a dialysis bag and placed in a 37° C. thermostat shaker (200 rpm). The former was immersed in 25 mL of PBS having the same GSH concentration at the same temperature, and the latter was immersed in 25 mL of PBS (20 mM) at the same temperature; after a given time period, 6 mL of dialysate outside the dialysis bag was taken to determine its fluorescence intensity, and 6 mL of a corresponding fresh solution was added to the outside of the dialysis bag.

Determination of drug loading efficiency of DOX in polymer nanoparticles: a certain amount of crosslinked and uncrosslinked drug-loaded nanoparticles solutions were taken, and the water in the solution was removed by a freeze-drying method; then 0.5 mL of formamide was added thereto, and the freeze-dried solid was fully fused with ultrasound for 1 h; 20 ml of the resulting solution was taken, to which 3 ml of formamide was added; after fluorescence test, the drug loading efficiency and dntg loading content were calculated with reference to a standard curve of doxorubicin.

Drug loading efficiency=(weight of loaded doxorubicin in nanoparticles/weight of doxorubicin in feed)×100%

Drug loading content=(weight of loaded doxorubicin in nanoparticles/total weight of the blank nanoparticles and doxorubicin in feed)×100%

When the theoretical drug loading content is 20%, the drug loading efficiency of HA-(aminohexylamino)-LA ($M_{nHA}$=400 kDa, DS=40%) crosslinked nanoparticles to doxorubicin was 79.8%, and the actual drug loading content was 15.96%.

The DOX-loaded crosslinked nanoparticles were rapidly decrosslinked in 10 mM GSH at 37° C. and about 83% DOX was released in 22 h; while DOX-loaded crosslinked nanoparticles were very stable in an environment free of GSH, and a little DOX was released, only 15%.

Example 48 DOX-Loaded HA-Aminoethylamino)-LA ($M_{nHA}$=37 kDa, DS=28%) Crosslinked Nanoparticles A solution of HA-(aminoethylamino)-LA ($M_{nHA}$=37 kDa, DS=28%)/formamide (5 mg/mL, 1 mL) was mixed with doxorubicin (DOX)/dimethylsulfoxide (5 mg/mL, 0.25 mL) under stirring for 1 h, and 4 ml of PBS was added dropwise to the mixture under stirring at 25° C., After being stirred for 1 h, the resulting solution was loaded into a previously prepared dialysis bag (SPECTRA/POR, MWCO: 3500) and dialyzed against PBS, to form a solution of drug-loaded polymer nanoparticles.

The formed drug-loaded polymer nanoparticle solution was taken in half volume and was adjusted to pH 8.5. 17.5 mL of 1 mg/mL 1,4-dithio-D,L-threobutanol (DTT) was added thereto after inletting of nitrogen gas for 10 minutes; the mixed solution was stirred for 24 h to undergo reaction at room temperature under nitrogen atmosphere. The crosslinked drug-loaded nanoparticles were dialyzed against PBS to remove the unreacted DTT.

The DOX-loaded crosslinked nanoparticles were 100-fold diluted with PBS (10 mM, pH 7.4) and divided into two portions: an equal volume of PBS of GSH (10 mM) was added to one portion, and an equal volume of pure PBS was added to the other portion at 37° C. These solutions were immediately transferred to a dialysis bag and placed in a 37° C. thermostat shaker (200 rpm). The former was immersed in of PBS having the same GSH concentration at the same temperature, and the latter was immersed in 25 mL of PBS (20 mM) at the same temperature; after a given time period, 6 mL of dialysate outside the dialysis bag was taken to determine its fluorescence intensity, and 6 mL of a corresponding fresh solution was added to the outside of the dialysis bag.

Determination of drug loading efficiency of DOX in polymer nanoparticles: a certain amount of crosslinked and uncrosslinked drug-loaded nanoparticles solutions were taken, and the water in the solution was removed by a freeze-drying method; then 0.5 mL of formamide was added thereto, and the freeze-dried solid was fully fused with ultrasound for 1 h; 20 ml of the resulting solution was taken, to which 3 ml of formamide was added; after fluorescence test, the drug loading efficiency and drug loading content were calculated with reference to a standard curve of doxorubicin.

Drug loading efficiency=(weight of loaded doxorubicin in nanoparticles/weight of doxorubicin in feed)×100%

Drug loading content=(weight of loaded doxorubicin in nanoparticles/total weight of the blank nanoparticles and doxorubicin in feed)×100%

When the theoretical drug loading content is 20%, the drug loading efficiency of HA-(aminoethylamino)-LA ($M_{nHA}$=37 kDa, DS=28%) crosslinked nanoparticles to doxorubicin was 63.5%, and the actual drug loading content was 12.7%.

The DOX-loaded crosslinked nanoparticles were rapidly decrosslinked in 10 mM GSH at 37° C. and about 82% DOX was released in 22 h; while DOX-loaded crosslinked nanoparticles were very stable in an environment free of GSH, and a little DOX was released, only 16%.

Biological Determination

Example 49 Intracellular Drug Release of DOX-Loaded Crosslinked Nanoparticles

Confocal laser scanning microscopy was used to observe endocytosis and intracellular release behaviors of DOX-loaded HA-Lys-LA ($M_{nHA}$=35 kDa. DS=10%, DLC=12%) in DOX-resistant human breast cancer cells (MCF-7/ADR) which expressed a high level of CD44 receptors and had resistance to DOX, MCF-7/ADR cells were first plated in cell culture plates at a density of $1\times10^5$/well and cultured at 37° C. with 5% carbon dioxide in 1 mL 1640 medium containing 10% serum, 100 IU mL of antibiotic penicillin and 10 µg/mL streptomycin for 24 h to achieve a monolayer coverage of cells of 70%. Then, 200 µL of DOX-loaded HA-Lys-LA crosslinked nanoparticles or free DOX solution was added to each well, wherein the final concentration of DOX in the wells was 5 µg/mL. After incubation at 37° C. with 5% carbon dioxide for 10 h, the medium was removed, and the suspensions were washed with PBS for three times, followed by fixation with 4% paraformaldehyde solution for 15 minutes and washed with PBS three times. Next, the cytoskeleton was stained with FITC-labeled phalloidin peptides and washed with PBS three times. Finally, the cell nucleus were stained with DAPI (4',6-diamidino-2-phenylindole dihydrochloride) for 15 minutes and washed with PBS three times. In receptor blocking experiment, a free HA solution (5 mg/mL) was incubated with the cells for 4 h prior to the addition of DOX-loaded HA-Lys-LA crosslinked nanoparticles, followed by steps as described above. The prepared sample was observed and photographed by confocal laser scanning microscopy.

Figure 4:
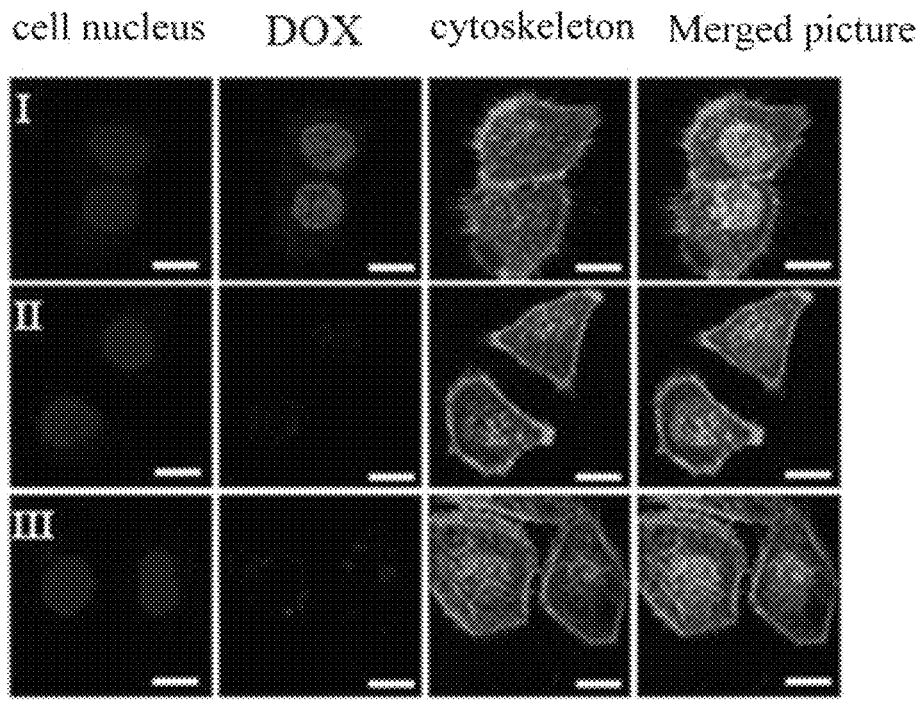
FIG. 4 is a picture showing the drug release results of a drug-loaded HA-Lys-LA crosslinked nanoparticles, DOX, and HA-encapsulated crosslinked nanoparticles in MCF-7/ADR cells (human breast cancer cells)

FIG. 4 is a picture showing the drug release results of a drug-loaded HA-Lys-LA crosslinked nanoparticles, DOX, and HA-encapsulated crosslinked nanoparticles in MCF-7/ADR cells (human breast cancer cells) (I represents the drug-loaded nanoparticles, II represents a free drug, and III represents a drug-loaded nanoparticles encapsulated with a free HA). As shown by the results, the DOX-loaded HA-Lys-LA crosslinked nanoparticles could be rapidly endocytosed by cells and release DOX in cells. After incubation for 10 h, almost all of the intracellular DOX fluorescence came into the nucleus, and the strength was significantly higher than control groups of free DOX and that encapsulated with a free HA, indicating that the nanoparticles had significant targeting property and capability of reversing drug resistance of tumor cells.

Example 50 Measurement of Cytotoxicity of A-Lys-LA Nanoparticles to MCF-7/ADR

Cytotoxicity of HA-Lys-LA blank nanoparticles (without loading any drug) ($M_{nHA}$=35 kDa, DS=5%, 10%, 28%) to MCF-7/ADR was measured by an MTT method. At first, 100 µL of a 1640 suspension of cells (the 1640 medium contained 10% fetal bovine serum, 100 Iu/mL penicillin and 100 µg/mL, streptomycin) was plated in a 96-well culture plate so that the final density of the cells was $1\times10^4$/well, and placed at 37° C., 5% carbon dioxide to perform incubation for 24 h so that the coverage of monolayer cells was 70 to 80%. Then, 20 µL of solution of different concentrations of HA-Lys-LA crosslinked or uncrosslinked nanoparticles in PBS were added to each well so that the final concentration of blank nanoparticles in the cell wells was 0.5 or 1.0 mg/mL. After incubation for 24 h, 20 µL of a solution of 3-(4,5-dimethylthiazol-2)-2,5-diphenyltetrazolium bromide (MTT) in PBS (5 mg/mL) was added to each well and incubated for 4 h in an incubator to allow MTT to interact with viable cells. The culture medium containing MTT was then removed, 150 µL DMSO was added to each well to dissolve the purple formazan crystals produced by viable cells and MTT, and the absorbance at 570 nm of each well was measured using a microplate reader (BioTek). The relative cell viability was obtained by comparing with the absorption at 570 nm of the control wells with only blank cells. The experimental data were obtained from four parallel groups.

Cell viability (%)=(OD570 sample/OD570 control)×100%

The anticancer activity of DOX-loaded HA-Lys-LA nanoparticles ($M_{nHA}$=35 kDa; DS=5%, 10%, 28%; DLC=11%, 12%, 15%) was measured by a method similar to the above-mentioned method of measuring cytotoxicity of blank nanoparticles. 100 µL of a 1640 suspension of MCF-7/ADR cells was plated in a 96-well culture plate so that the final density of the cells was $1\times10^4$/well, and placed at 37° C., 5% carbon dioxide to perform incubation for 24 h so that the coverage of monolayer cells was 70 to 80%. Then, 20 µL of solution of DOX-loaded HA-Lys-LA crosslinked or uncrosslinked nanoparticles having different degree of substitution or free DOX in PBS were added to each well so that the final concentration of DOX in the cell wells was 0.0023 to 150 µg/mL. After incubation for 4 h. the original medium was removed, and the same amount of fresh medium was added. After incubation for 44 h, 20 µL of a MTT solution (5 mg/mL) was added to each well and incubated for 4 h in an incubator. The subsequent assay and toxicity measurement were the same as described above. In receptor blocking experiment, the free HA solution (5 mg/mL) was incubated with cells for 4 h before addition of DOX-loaded HA-Lys-LA crosslinked nanoparticles, to complete the blocking of tumor cells by HA. Next steps are the same as the above, as control groups.

Figure 5:
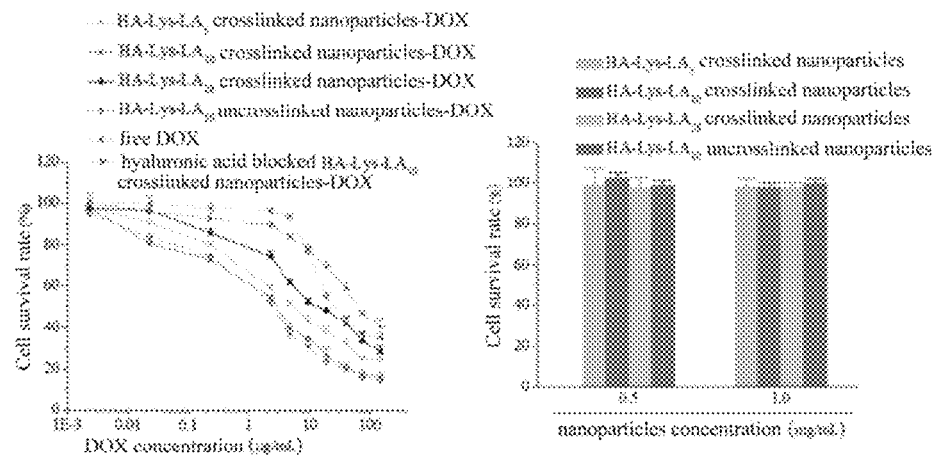
FIG. 5 is a graph showing results of the cytotoxicity of different HA-Lys-LA nanoparticles to MCF-7/ADR cells in Example 50.

FIG. 5 is a graph showing results of the cytotoxicity of different HA-Lys-LA nanoparticles to MCF-7/ADR cells. As shown by the results, HA-Lys-LA crosslinked nanoparticles had good biocompatibility, and DOX-loaded crosslinked nanoparticles had antitumor activity and had the highest anti-tumor activity when the degree of substitution was 10%, because the formed crosslinked nanoparticles were not stable in case of a too low degree of substitution and excessive modification to hyaluronic acid would affect its targeting ability.

Example 51 Measurement of Cytotoxicity of HA-Lys-LA Nanoparticles to MCF-7/ADR

Cytotoxicity of HA-Lys-LA blank nanoparticles ($M_{nHA}$=35 kDa, DS=40%) to MCF-7/ADR was measured by an MTT method. At first, 100 μL of a 1640 suspension of cells (the 1640 medium contained 10% fetal bovine serum, 100 Iu mL penicillin and 100 μg/mL streptomycin) was plated in a 96-well culture plate so that the final density of the cells was 1×10$^4$/well, and placed at 37° C., 5% carbon dioxide to perform incubation for 24 h so that the coverage of monolayer cells was 70 to 80%. Then, 20 μL of solution of different concentrations of HA-Lys-LA crosslinked or uncrosslinked nanoparticles in PBS were added to each well so that the final concentration of blank nanoparticles in the cell wells was 0.5 or 1.0 mg/mL. After incubation for 24 h, 20 μL of a solution of 3-(4,5-dimethylthiazol-2)-2,5-diphenyltetrazolium bromide (MTT) in PBS (5 mg/mL) was added to each well and incubated for 4 h in an incubator to allow MTT to interact with viable cells. The culture medium containing MTT was then removed, 150 μL DMSO was added to each well to dissolve the purple formazan crystals produced by viable cells and MTT, and the absorbance at 570 nm of each well was measured using a microplate reader (BioTek). The relative cell viability was obtained by comparing with the absorption at 570 nm of the control wells with only blank cells. The experimental data were obtained from four parallel groups.

Cell viability (%)=($OD$570 sample/$OD$570 control)× 100%

The anticancer activity of DOX-loaded HA-Lys-LA nanoparticles ($M_{nHA}$=35 kDa; DS=40%; DLC=20%) was measured by a method similar to the above-mentioned method of measuring cytotoxicity of blank nanoparticles. 100 μL of a 1640 suspension of MCF-7/ADR cells was plated in a 96-well culture plate so that the final density of the cells was 1*10$^4$/well, and placed at 37° C., 5% carbon dioxide to perform incubation for 24 h so that the coverage of monolayer cells was 70 to 80%. Then, 20 μL of solution of DOX-loaded HA-Lys-LA crosslinked or uncrosslinked nanoparticles having different degree of substitution or free DOX in PBS were added to each well so that the final concentration of DOX in the cell wells was 0.0023 to 150 μg/mL, After incubation for 4 h, the original medium was removed, and the same amount of fresh medium was added. After incubation for 44 h, 20 μL of a MTT solution (5 mg/mL) was added to each well and incubated for 4 h in an incubator. The subsequent assay and toxicity measurement were the same as described above. In receptor blocking experiment, the free HA solution (5 mg/mL) was incubated with cells for 4 h before addition of DOX-loaded HA-Lys-LA crosslinked nanoparticles, to complete the blocking of tumor cells by HA. Next steps are the same as the above, as control groups.

As shown by the results, blank HA-Lys-LA crosslinked nanoparticies had good biocompatibility, and the DOX-loaded crosslinked nanoparticles had certain antitumor activity.

Example 52 Measurement of Cytotoxicity to Human Glioma (U87MG)

Cytotoxicity of HA-Lys-LA blank nanoparticles ($M_{nHA}$=35 kDa, DS=5%, 10%, 28%) to U87MG cells was measured by an MTT method. At first, 100 μL of a DMEM low glucose medium of cells (the DMEM low glucose medium contained 10% fetal bovine serum, 100 IU/mL penicillin and 100 g/mL streptomycin) was plated in a 96-well culture plate so that the final density of the cells was 1×10$^4$/well, and placed at 37° C., 5% carbon dioxide to perform incubation for 24 h so that the coverage of monolayer cells was 70 to 80%. Then, 20 μL of solution of different concentrations of HA-Lys-LA crosslinked or uncrosslinked nanoparticies in PBS were added to each well so that the final concentration of blank nanoparticles in the cell yells was 0.5 or 1.0 mg/mL. After incubation for 24 h, 20 μL of a solution of 3-(4,5-dimethylthiazol-2)-2,5-diphenyltetrazolium bromide (MTT) in PBS (5 mg/mL) was added to each well and incubated for 4 h in an incubator to allow MTT to interact with viable cells. The culture medium containing MTT was then removed, 150 μL DMSO was added to each well to dissolve the purple formazan crystals produced by viable cells and MTT, and the absorbance at 570 nm of each well was measured using a microplate reader (BioTek). The relative cell viability was obtained by comparing with the absorption at 570 nm of the control wells with only blank cells. The experimental data were obtained from four parallel groups.

Cell viability (%)=($OD$570 sample/$OD$570 control)× 100%

The anticancer activity of DOX-loaded HA-Lys-LA nanoparticles ($M_{nHA}$=35 kDa; DS=5%, 10%, 28%; DLC=11%, 12%, 15%) was measured by a method similar to the above-mentioned method of measuring cytotoxicity of blank nanoparticles. 100 μL of a DMEM low glucose medium of U87MG cells was plated in a 96-well culture plate so that the final density of the cells was 1×10$^4$/well, and placed at 37° C., 5% carbon dioxide to perforin incubation for 24 h so that the coverage of monolayer cells was 70 to 80%. Then, 20 μL of solution of DOX-loaded HA-Lys-LA crosslinked or uncrosslinked nanoparticles having different degree of substitution or free DOX in PBS were added to each well so that the final concentration of DOX in the cell wells was 0.0023 to 150 μg/mL. After incubation for 4 h, the original medium was removed, and the same amount of fresh medium was added. After incubation for 44 h, 20 μL of a MTT solution (5 mg/mL) was added to each well and incubated for 4 h in an incubator. The subsequent assay and toxicity measurement were the same as described above. In receptor blocking experiment, the free HA solution (5 mg/mL) was incubated with cells for 4 h before addition of DOX-loaded HA-Lys-LA crosslinked nanoparticles, to complete the blocking of tumor cells by HA. Next steps are the same as the above.

As shown by the results, the cell viability of blank nanoparticles in U87MG cells after 48 h was more than 90%, which indicated that the biocompatibility of blank nanoparticles was good. DOX-loaded HA-Lys-LA cross-linked nanoparticles had antitumor activity in U87MG cells with low expression of CD44 receptor, but drug-loaded nanoparticles having different degrees of substitution were close in antitumor activity, which was far lower than that of the free drug.

Example 52 Measurement of Cytotoxicity to Human Glioma (U87MG)

Cytotoxicity of HA-Lys-LA blank nanoparticles ($M_{nHA}$=35 kDa, DS=40%) to U87MG cells was measured by an MTT method. At first, 100 μL of a DMEM low glucose medium of cells (the DMEM low glucose medium contained 10% fetal bovine serum, 100 IU/mL penicillin and 100 μL streptomycin) was plated in a 96-well culture plate so that the final density of the cells was $1\times10^4$/well, and placed at 37° C., 5% carbon dioxide to perform incubation for 24 h so that the coverage of monolayer cells was 70 to 80%. Then, 20 μL of solution of different concentrations of HA-Lys-LA crosslinked or uncrosslinked nanoparticles in PBS were added to each well so that the final concentration of blank nanoparticles in the cell wells was 0.5 or 1.0 mg/mL. After incubation for 24 h, 20 μL of a solution of 3-(4,5-dimethylthiazol-2)-2,5-diphenyltetrazolium bromide (MTT) in PBS (5 mg/mL) was added to each well and incubated for 4 h in an incubator to allow MTT to interact with viable cells. The culture medium containing MTT was then removed, 150 μL DMSO was added to each well to dissolve the purple formazan crystals produced by viable cells and MTT, and the absorbance at 570 nm of each well was measured using a microplate reader (BioTek). The relative cell viability was obtained by comparing with the absorption at 570 nm of the control wells with only blank cells. The experimental data were obtained from four parallel groups.

Cell viability (%)=(OD570 sample/OD570 control)×100%

The anticancer activity of DOX-loaded HA-Lys-LA nanoparticles ($M_{nHA}$=35 kDa; DS=40%; DLC=20%) was measured by a method similar to the above-mentioned method of measuring cytotoxicity of blank nanoparticles. 100 μL of a DMEM low glucose medium of U87MG cells was plated in a 96-well culture plate so that the final density of the cells was $1\times10^4$/well, and placed at 37° C., 5% carbon dioxide to perform incubation for 24 h so that the coverage of monolayer cells was 70 to 80%. Then, 20 μL of solution of DOX-loaded HA-Lys-LA crosslinked or uncrosslinked nanoparticles having different degree of substitution or free DOX in PBS were added to each well so that the final concentration of DOX in the cell wells was 0.002.3 to 150 μg/mL. After incubation for 4 h, the original medium was removed, and the same amount of fresh medium was added. After incubation for 44 h, 20 μL of a MTT solution (5 mg/mL) was added to each well and incubated for 4 h in an incubator. The subsequent assay and toxicity measurement were the same as described above. In receptor blocking experiment, the free HA solution (5 mg/mL) was incubated with cells for 4 h before addition of DOX-loaded HA-Lys-LA crosslinked nanoparticles, to complete the blocking of tumor cells by HA. Next steps are the same as the above.

As shown by the results, the cell viability of blank nanoparticles in U87MG cells after 48 h was more than 88%, which indicated that the biocompatibility of blank nanoparticles was good. DOX-loaded. HA-Lys-LA crosslinked nanoparticles had antitumor activity in U87MG cells with low expression of CD44 receptor, but drug-loaded nanoparticles having different degrees of substitution were close in antitumor activity, which was far lower than that of the free drug.

Example 54 Study of Circulation of DOX-Loaded HA-Lys-LA Crosslinked Nanoparticles in the Body of Mice The following animal test operations were carried out under protocols approved by Soochow University Laboratory Animal Center. Six about 5-8 weeks old nude mice weighing 18-22 g were randomly divided into two groups, and each group was administered with DOX-loaded HA-Lys-LA crosslinked nanoparticles ($M_{nHA}$=35 kDa, DS=10%, DLC=12%) or free DOX (DOX dosage being 15 mg/kg) via tail vein injection. 10 μL of blood was withdrawn from the tail vein each time at different time points after injection for 2 minutes, 15 minutes, 30 minutes, 1 h, 2 h, 4 h, 6 h, 8 h, 12 h, 24 h. After the blood was withdrawn, the blood sample was weighed and dissolved in 100 μL of 1% Triton solution, and then 1 mL of 0.75 mol/L hydrochloric acid isopropanol solution was added thereto. The mixture was allowed to stand overnight in dark at −20° C. After centrifugation, the supernatant was subjected to fluorescence test.

% ID/g=(FL sample×(V Triton+V hydrochloric acid))/(M blood×FL standard×V standard×standard dilution factor)×100%

Figure 6:
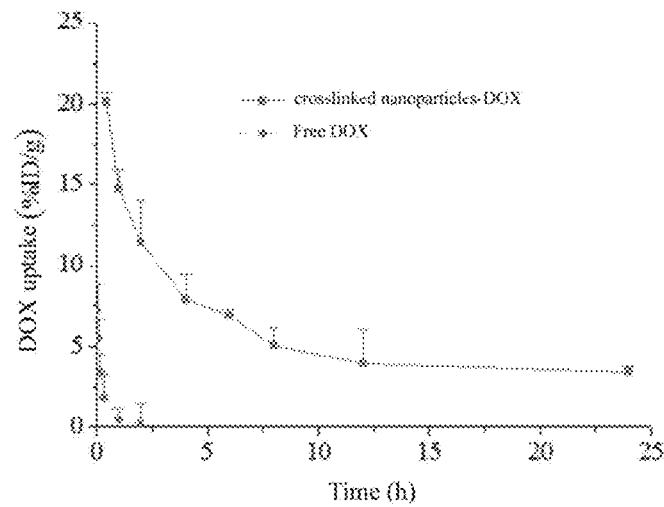
FIG. 6 is a graph showing results of blood circulation of DOX-loaded HA-Lys-LA crosslinked nanoparticles in mice in Example 54.

FIG. 6 is a graph showing results of blood circulation of DOX-loaded HA-Lys-LA crosslinked nanoparticles ($M_{nHA}$=35 kDa, DS=10%, DLC=12%) in mice. As shown by the results, the DOX-loaded HA-Lys-LA crosslinked nanoparticles had good stability and could achieve long circulation in mice, while free DOX was almost not detected in mice blood after 2 h.

Example 55 Study of Circulation of DOX-Loaded HA-Lys-LA Crosslinked Nanoparticles in the Body of Mice The following animal test operations were carried out under protocols approved by Soochow University Laboratory Animal Center. Six about 5-8 weeks old nude mice weighing 18-22 g were randomly divided into two groups, and each group was administered with DOX-loaded HA-Lys-LA crosslinked nanoparticles ($M_{nHA}$=35 kDa, DS=40%, DLC=20%) or free DOX (DOX dosage being 15 mg/kg) via tail vein injection. 10 μL of blood was withdrawn from the tail vein each time at different time points after injection for 2 minutes, 15 minutes, 30 minutes, 1 h, 2 h, 4 h, 6 h, 8 h, 12 h, 24 h. After the blood was withdrawn, the blood sample was weighed and dissolved in 100 μL of 1% Triton solution, and then 1 mL of 0.75 mol/L hydrochloric acid isopropanol solution was added thereto. The mixture was allowed to stand overnight in dark at −20° C. After centrifugation, the supernatant was subjected to fluorescence test.

% ID/g=(FL sample×(V Triton+V hydrochloric acid))/(M blood×FL standard×V standard×standard dilution factor)×100%

As shown by the results, the DOX-loaded HA-Lys-LA crosslinked nanoparticles ($M_{nHA}$=35 kDa, DS=40%, DLC=20%) had good stability and could achieve long circulation in mice, while free DOX was almost not detected in mice blood after 2 h.

Example 56 In Vivo Imaging of Nude Mice Bearing a Drug-Resistant Breast-Cancer Tumor Treated with HA-Lys-LA Crosslinked Nanoparticles Distribution of HA-Lys-LA crosslinked nanoparticles ($M_{nHA}$=35 kDa, DS=10%) at respective parts was observed in real time by using a Maestro in vivo imaging system during in vivo circulation. Xenograft model of nude mice bearing drug-resistant breast-cancer tumor was established by subcutaneous inoculation of 1×10$^7$ MCF-7/ADR into the hind flank of each nude mice (weighing 18 to 22 g). When the size of tumors reached 100 mm$^3$, the tumor-bearing nude mice were injected with 0.2 mL of a solution of fluorescent molecule Cy7-loaded HA-Lys-LA crosslinked nanoparticle via tail vein. Then, the nude mice were anesthetized at a certain time point and fixed on a black plastic plate, placed in a Maestro in vivo imaging system, and the intensity of Cy7 distribution in vivo was measured at an emission wavelength of 720 nm.

Figure 7:
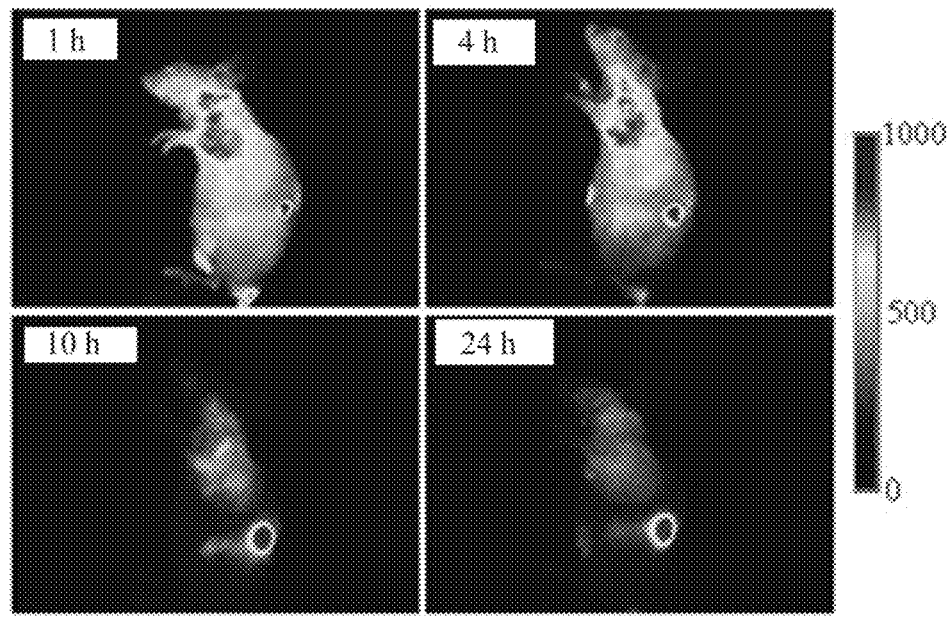
FIG. 7 is a picture showing results of in vivo imaging of Cy7-loaded HA-Lys-LA crosslinked nanoparticles in MCF-7/ADR tumor-bearing nude mice in Example 54.

FIG. 7 is a picture showing results of in vivo imaging of Cy7-loaded HA-Lys-LA crosslinked nanoparticles in tumor-bearing nude mice. As shown by the results, the fluorescence intensity of Cy7 in nude mice increased with the prolongation of time, and the fluorescence intensity at tumor sites was the strongest at 10 h, and the Cy7 fluorescence at tumor sites was still strong after 24 h, indicating that HA-Lys-LA crosslinked nanoparticles could effectively enrich at the tumor sites and maintain a long time.

Example 57 Ex Vivo Imaging of Organs of Nude Mice Bearing a Drug-Resistant Breast-Cancer Tumor Treated with DOX-Loaded HA-Lys-LA Crosslinked Nanoparticles Six nude mice bearing drug-resistant breast-cancer tumor with a tumor size of 100 mm$^3$ were randomly divided into two groups, and each mice was administratated intravenously via the tail vein with 0.2 mL of (1) DOX-loaded HA-Lys-LA crosslinked nanoparticles ($M_{nHA}$=35 kDa, DS=10%, DLC=12%); (2) a free DOX solution (a final DOX concentration of about 15 mg/kg). After 10 h, the heart, liver, spleen, lung, kidney and tumor block were collected, washed and fixed on a black plastic plate, which was then placed in a Maestro in vivo imaging system, and the intensity of DOX distribution in vivo was measured at an emission wavelength of 523 nm.

As shown by the results, DOX-loaded HA-Lys-LA crosslinked nanoparticles ($M_{nHA}$=35 kDa, DS=10%, DLC=12%) concentrated at the tumor site more than other organs and released strong DOX fluorescence, while free DOX almost did not concentrate at the tumor site.

Example 58 Bio-Distribution of DOX-Loaded HA-Lys-LA Crosslinked Nanoparticles in Organs of Nude Mice Bearing a Drug-Resistant Breast-Cancer Tumor Six tumor-bearing nude mice with a tumor size of 100 mm$^3$ were randomly divided into two groups, and each mice was administratated intravenously via the tail vein with 0.2 mL of (1) DOX-loaded HA-Lys-LA crosslinked nanoparticles ($M_{nHA}$=35 kDa, DS=10%, DLC=12%); (2) a free DOX solution (a final DOX concentration of about 15 mg/kg). After 10 h, the heart, liver, spleen, lung, kidney and tumor block were collected, washed, weighed, and then 400 µL of 1% Triton was added thereto; the resultant was homogenized with a homogenizer, and then 600 µL of 0.75 mol/L of hydrochloric acid isopropanol solution was added thereto. The mixture was placed in a −20° C. refrigerator. After 24 h, the mixture was subjected to centrifugation, and the supernatant was subjected to fluorescence test.

% ID/g=(FL organ×(V treatment solution+V organ))/(V drug×dilution factor×FL drug×M organ)×100%

Figure 8:
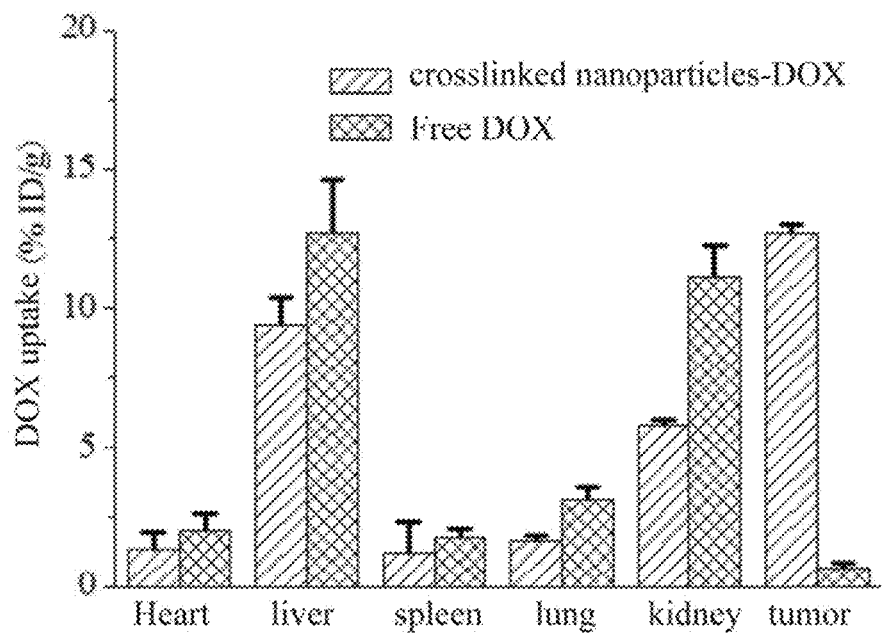
FIG. 8 is a graph showing results of bio-distribution of DOX-loaded HA-Lys-LA crosslinked nanoparticles in organs of MCF-7/ADR tumor-bearing nude mice in Example 58.

FIG. 8 is a graph showing results of bio-distribution of DOX-loaded HA-Lys-LA crosslinked nanoparticles ($M_{nHA}$=35 kDa, DS=10%, DLC=12%) in organs of tumor-bearing nude mice. As shown by the results, the DOX-loaded HA-Lys-LA crosslinked nanoparticles has a high enrichment of 12.71% ID/g at the tumor site, while a little free DOX concentrated at the tumor site, only 0.63% ID/g. After intravenous injection via the tail vein of existing doxorubicine (DOX)-loaded hollow gold nanoparticles with the surface modified with polyethylene glycol (PEG) for 6 h and 24 h, DOX concentration at the tumor site was less than 5% ID/g, which indicates that the drug carrier based on the hyaluronic acid amphiphilic polymer of the present invention can effectively enter the tumor cells without modifying the target molecule, and the enrichment ratio at the tumor site is high.

Example 59 Anti-Tumor Effect of DOX-Loaded HA-Lys-LA Crosslinked Nanoparticles in Nude Mice Bearing Drug-Resistant Breast-Cancer Tumor Tumor-bearing nude mice with a tumor size of 50 mm$^3$ were randomly divided into three groups (six in each group), and this day is set to day 0. Each mice was administratated intravenously via the tail vein with 0.2 mL of (1) DOX-loaded HA-Lys-LA crosslinked nanoparticles ($M_{nHA}$=35 kDa, DS=10%, DLC=12%); (2) a free DOX solution; (3) PBS (a final DOX concentration of about 7.5 mg/kg). Effects of drug-loaded micelles on tumor growth in nude mice were regularly measured with a caliper. Changes in body weight of nude mice were regularly weighed with a balance. The tumor size was obtained based on a formula V=0.5×L×W×H is the length of the longest points of the tumor; W is the length of the shortest points of the tumor; H is the height of the tumor). After 24 days, one mouse was randomly taken from each group and was killed by neck and spine dislocation, and the heart, liver and tumor of each mouse were removed and fixed with 4% formaldehyde, sliced and stained with hematoxylin and eosin (H & E) and subjected to histological analysis. The remaining nude mice were still observed. Mice were considered to be died when the nude mice died during treatment, or the tumor volume exceeded 1000 mm$^3$.

Relative tumor volume (%)=tumor volume/tumor volume on day 0×100%.

Relative weight change (%)=body weight of nude mice/body weight of nude mice on day 0×100%.

Figure 9:
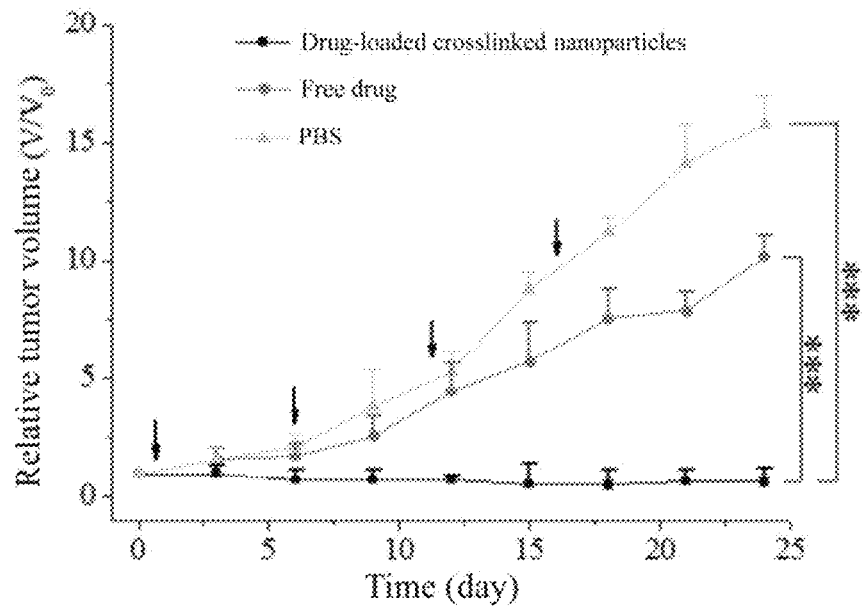
FIG. 9 is a graph showing results of tumor growth changes in MCF-7/ADR tumor-bearing nude mice treated with DOX-loaded HA-Lys-LA crosslinked nanoparticles in Example 59.
Figure 10:
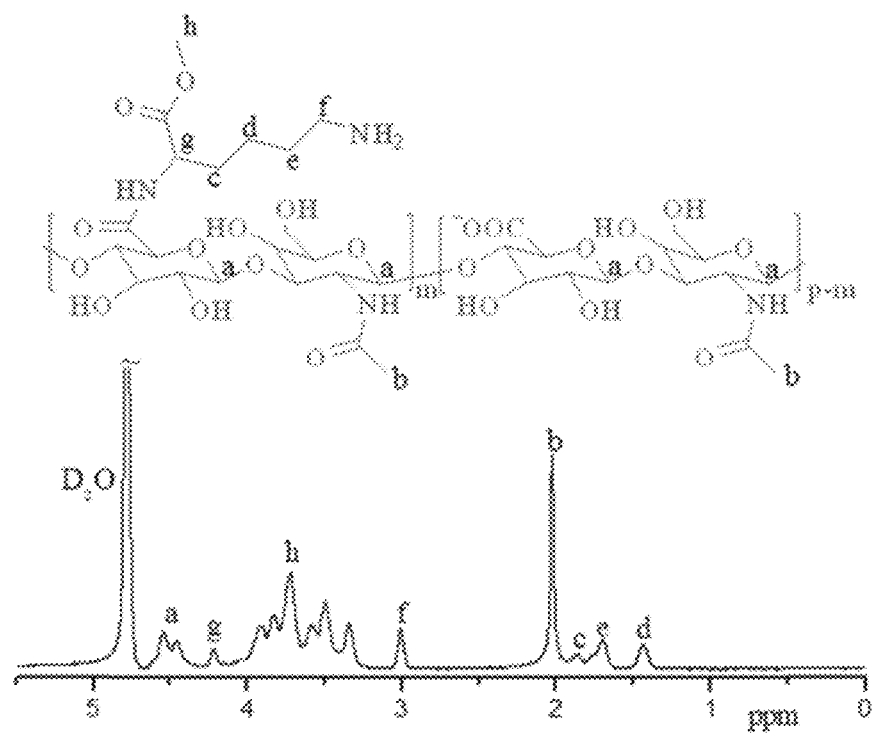
FIG. 10 shows a structural formula of an HA-Lys conjugate and its $^1$H NMR (400 MHz, $D_2O$) spectra.

FIG. 9 is a graph showing results of tumor growth changes in tumor-bearing nude mice treated with DOX-loaded HA-Lys-LA crosslinked nanoparticles ($M_{nHA}$=35 kDa, DS=10%, DLC=12%). As shown by the results, DOX-loaded HA-Lys-LA crosslinked nanoparticles could effectively inhibit tumor volume growth and had high antitumor activity, while free DOX could not inhibit tumor growth. Changes in body weight of nude mice and survival experiment show that DOX-loaded HA-Lys-LA crosslinked nanoparticles ($M_{nHA}$=35 kDa, DS=10%, DLC=12%) had no effect on body weight, less side effects, and resulted in the longest survival time, while free DOX reduced the body weight of nude mice by 28%, had large side effects, and caused all mice to die within 28 days. Besides, as shown by results of H&E staining histological analysis, a tumor tissue corresponding to the DOX-loaded HA-Lys-LA crosslinked nanoparticles ($M_{nHA}$=35 kDa, DS=10%, DLC=12%) had a large area of necrosis, but the heart and liver were both normal; while the tumor tissues corresponding to free DOX and PBS groups grew vigorously, and the liver corresponding to the free DOX group was greatly damaged, and myocardial cell atrophied, and vacuoles appeared, accompanied with inflammatory tissue infiltration.

Example 60 Tumor Growth Effect of DOX-Loaded HA-Ornithine-LA ($M_{nHA}$=100 kDa, DS=28%) Crosslinked Nanoparticles in LP1 Tumor (Multiple Myeloma)-Bearing Nude Mice Tumor-bearing nude mice with a tumor size of 50 min³ were randomly divided into three groups (six in each group), and this day is set to day 0. Each mice was administrated intravenously via the tail vein with 0.2 mL of (1) DOX-loaded HA-Lys-LA crosslinked nanoparticles ($M_{nHA}$=100 kDa, DS=28%, DLC=12%); (2) a free DOX solution; (3) PBS (a final DOX concentration of about 7.5 mg/kg). Effects of drug-loaded micelles on tumor growth in nude mice were regularly measured with a caliper. Changes in body weight of nude mice were regularly weighed with a balance. The tumor size was obtained based on a formula V=0.5×L×W×H (L is the length of the longest points of the tumor; W is the length of the shortest points of the tumor; H is the height of the tumor). After 24 days, one mouse was randomly taken from each group and was killed by neck and spine dislocation, and the heart, liver and tumor of each mouse were removed and fixed with 4% formaldehyde, sliced and stained with hematoxylin and eosin (H & E) and subjected to histological analysis. The remaining nude mice were still observed. Mice were considered to be died when the nude mice died during treatment, or the tumor volume exceeded 1000 mm³.

Relative tumor volume (%)=tumor volume/tumor volume on day 0×100%.

Relative weight change (%)=body weight of nude mic body weight of nude mice on day 0×100%.

FIGS. 13A to 13D show results of tumor growth changes in tumor-bearing nude mice treated with DOX-loaded HA-omrnthine-LA crosslinked nanoparticles ($M_{nHA}$=100 kDa, DS=28%, DLC=12%). FIG. 13A shows relative tumor volume change results. From FIG. 13A, it can be seen that in mice treated with DOX-loaded HA-ornithine-LA crosslinked nanoparticles, ⅔ of tumors basically disappeared within 25 days. From FIG. 13B, it can be seen that as compared with mice treated with PBS, the tumor volume in mice treated with DOX-loaded HA-ornithine-LA crosslinked nanoparticles significantly decreased. FIG. 13C shows a relative change in body weight of nude mice. In view of FIG. 13C, free drug would cause great decrease in body weight of mice, while mice treated with DOX-loaded HA-ornithine-LA crosslinked nanoparticles had a relatively less change in body weight. In view of FIGS. 13 A and 13B, DOX-loaded HA-ornithine-LA crosslinked nanoparticles increased antitumor activity of mice while having less toxicity to mice. FIG. 13D shows a mice survival rate. As shown by results of FIGS. 13A to D, DOX-loaded HA-ornithine-LA crosslinked nanoparticles could effectively inhibit tumor volume growth and had high antitumor activity, while free DOX could not inhibit tumor growth. Changes in body weight of nude mice and survival experiment show that DOX-loaded HA-ornithine-LA crosslinked nanoparticles ($M_{nHA}$=100 kDa, DS=28%, DLC=12%) had no effect on body weight, less side effects, and resulted in the longest survival time, while free DOX reduced the body weight of nude mice by about 34%, had large side effects, and caused all mice to die within 15 days. Besides, as shown by results of H&E staining histological analysis, a tumor tissue corresponding to the DOX-loaded HA-ornithine-LA crosslinked nanoparticles ($M_{nHA}$=100 kDa, DS=28%, DLC=12%) had a large area of necrosis, but the heart and liver were both normal; while the tumor tissues corresponding to free DOX and PBS groups grew vigorously, and the liver corresponding to the free DOX group was greatly damaged, and myocardial cell atrophied, and vacuoles appeared, accompanied with inflammatory tissue infiltration.

Example 61 Study of Circulation of DOX-Loaded HA-Ornithine Methyl Ester-LA Crosslinked Nanoparticles in the Body of mice The following animal test operations were carried out under protocols approved by Soochow University Laboratory Animal Center. Six about 5-8 weeks old nude mice weighing 18-22 g were randomly divided into two groups, and each group was administered with DOX-loaded HA-ornithine methyl ester-LA crosslinked nanoparticles ($M_{nHA}$=35 kDa, DS=28%, DLC=12%) or free DOX (DOX dosage being 15 mg/kg) via tail vein injection. 10 μL of blood was withdrawn from the tail each time at different time points after injection for 2 minutes, 15 minutes, 30 minutes, 1 h, 2 h, 4 h, 6 h, 8 h, 12 h, 24 h. After the blood was withdrawn, the blood sample was weighed and dissolved in 100 μL of 1% Triton solution, and then 1 mL of 0.75 mol/L hydrochloric acid isopropanol solution was added thereto. The mixture was allowed to stand overnight in dark at −20° C. After centrifugation, the supernatant was subjected to fluorescence test.

% ID/g=($FL$ sample×($V$ Triton+$V$ hydrochloric acid))/($M$ blood×$FL$ standard×$V$ standard×standard dilution factor)×100%

FIG. 14 is a graph showing results of blood circulation of DOX-loaded HA-ornithine methyl ester-LA crosslinked nanoparticles ($M_{nHA}$=35 kDa, DS=28%, DLC=12%) and DOX in mice. As shown by the results, the DOX-loaded HA-ornthine methyl ester-LA crosslinked nanoparticles had good stability and could achieve long circulation in mice, while free DOX was almost not detected in mice blood after 2 h.

Example 62 Bio-Distribution of DOX-Loaded HA-(aminohexylamino)-LA ($M_{nHA}$=400 kDa, DS=40%) Crosslinked Nanoparticles in Organs of Nude Mice Bearing a Drug-Resistant Breast-Cancer Tumor Six tumor-bearing nude mice with a tumor size of 100 mm³ were randomly divided into two groups, and each nude mice was administrated intravenously via the tail vein with 0.2 mL of (1) DOX-loaded HA-(aminohexylamino)-LA crosslinked nanoparticles ($M_{nHA}$=400 kDa, DS=40%, DLC=12%); (2) a free DOX solution (a final DOX concentration of about 15 mg/kg). After 10 h, the heart, liver, spleen, lung, kidney and tumor block were collected, washed, weighed, and then 400 μL of 1% Triton was added thereto; the resultant was homogenized with a homogenizer, and then 600 μL of 0.75 mol/L of hydrochloric acid isopropanol solution was added thereto. The mixture was placed in a −20° C. refrigerator. After 24 h, the mixture was subjected to centrifugation, and the supernatant was subjected to fluorescence test.

% ID/g=(FL organ×(V treatment solution+V organ))/(V drug×dilution factor×FL drug×M organ)×100%

FIG. 15 is a graph showing results of bio-distribution of DOX-loaded HA-(aminohexylamino)-LA crosslinked nanoparticles ($M_{nHA}$=35 kDa, DS=10%, DLC=12%) in organs of tumor-bearing nude mice. As shown by the results, the DOX-loaded HA-(aminohexylamino)-LA crosslinked nanoparticles has a high enrichment of 15.3% ID/g at the tumor site, while a little free DOX concentrated at the tumor site, only 0.63% ID/g. After intravenous injection via the tail vein of existing doxorubicine (DOX)-loaded hollow gold nanoparticles with the surface modified with polyethylene glycol (PEG) for 6 h and 24 h, DOX concentration at the tumor site was less than 5% ID/g, Which indicates that the drug carrier based on the hyaluronic acid amphiphilic polymer of the present invention can effectively enter the tumor cells without modifying the target molecule, and the enrichment ratio at the tumor site is high.

What is claimed is:

1. A hyaluronic acid-based amphiphilic polymer of which a main chain is hyaluronic acid, and a side chain is lysine methyl ester-lipoyl, the side chain having a structural formula as follows:

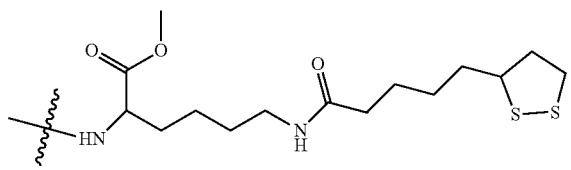 [SMILES: *NC(CCCCNC(=O)CCCCC1CCSS1)C(=O)OC]

wherein the hyaluronic acid has a molecular weight of 7 to 500 kDa; and the degree of substitution of the side chain is from 5 to 40%.

2. A method of preparing the hyaluronic acid-based amphiphilic polymer according to claim 1, which comprises the following steps:

first, under the catalysis of 1-(3-dimethylaminopropyl)-3-ethylcarbodiimide hydrochloride/N-hydroxysuccinimide, reacting hyaluronic acid with N-tert-butoxycarbonyl lysine methyl ester through an amidation reaction to obtain hyaluronic acid-N-tert-butoxycarbonyl lysine methyl ester;

second, deprotecting, to obtain hyaluronic acid-lysine methyl ester;

third, reacting hyaluronic acid-lysine methyl ester with lipoic acid anhydride through an amidation reaction under catalysis of 4-(dimethylamino) pyridine, to obtain the hyaluronic acid-based amphiphilic polymer according to claim 1.

3. A crosslinked nanoparticle having an outer hydrophilic layer and an inner hydrophobic layer, wherein the crosslinked nanoparticle is composed of the amphiphilic polymer according to claim 1, the outer hydrophilic layer of the crosslinked nanoparticle is composed of the hyaluronic acid portion of the polymer according to claim 1, and the inner hydrophobic layer of the crosslinked nanoparticle is composed of crosslinked five-membered ring moieties of the lysine methyl ester-lipoyl side chains as set forth in claim 1.

4. A drug-loaded nanoparticle, comprising an amphiphilic polymer according to claim 1 and a small molecule anticancer drug loaded on the polymer.

5. A drug-loaded nanoparticle, comprising a carrier and a small molecule anticancer drug, wherein said carrier is composed of the amphiphilic polymer according to claim 1, wherein the nanoparticle has an outer hydrophilic layer composed of the hyaluronic acid portion of the polymer according to claim 1, and wherein the nanoparticle has an inner hydrophobic layer composed of crosslinked five-membered ring moieties of the lysine methyl ester-lipoyl side chains as set forth in claim 1.

6. The drug-loaded nanoparticle according to claim 5, wherein the small molecule anticancer drug is doxorubicin, paclitaxel, curcumin, docetaxel, or camptothecin.

7. The drug-loaded nanoparticle according to claim 5, wherein the loading efficiency of the carrier to the small molecule anticancer drug is 40% to 91%, and the drug loading content of the drug-loaded nanoparticles is 11% to 22%.

8. The drug-loaded nanoparticle according to claim 5, wherein the particle size of the drug-loaded nanoparticles is 50-300 nm.

9. A method for treating a tumor in a human or animal, the method comprising administering to a human or animal in need of treatment for a tumor a therapeutically effective amount of the drug-loaded nanoparticles according to claim 5.

10. The method according to claim 9, wherein the tumor is a tumor in which CD44 receptors are overexpressed.

11. A drug carrier which is the amphiphilic polymer according to claim 1.

* * * * *